(12) United States Patent
Zarling et al.

(10) Patent No.: US 8,466,130 B2
(45) Date of Patent: Jun. 18, 2013

(54) MITOCHONDRIA TARGETED CATIONIC ANTI-OXIDANT COMPOUNDS FOR PREVENTION, THERAPY OR TREATMENT OF HYPER-PROLIFERATIVE DISEASE, NEOPLASIAS AND CANCERS

(75) Inventors: David A. Zarling, Menlo Park, CA (US); Hirak S. Basu, Madison, WI (US); Balaraman Kalyanaraman, Wauwatosa, WI (US); Joy Joseph, New Berlin, WI (US)

(73) Assignees: Colby Pharmaceutical Company, Menlo Park, CA (US); Medical College of Wisconsin, Inc., Milwaukee, WI (US)

( * ) Notice: Subject to any disclaimer, the term of this patent is extended or adjusted under 35 U.S.C. 154(b) by 618 days.

(21) Appl. No.: 12/554,476

(22) Filed: Sep. 4, 2009

(65) Prior Publication Data

US 2011/0059922 A1    Mar. 10, 2011

(51) Int. Cl.
| | |
|---|---|
| *A01N 57/00* | (2006.01) |
| *A01N 33/24* | (2006.01) |
| *A61K 31/675* | (2006.01) |
| *A61K 31/13* | (2006.01) |
| *C07C 239/00* | (2006.01) |
| *C07C 259/00* | (2006.01) |
| *C07F 9/02* | (2006.01) |

(52) U.S. Cl.
USPC .................. 514/89; 514/645; 564/300; 568/9

(58) Field of Classification Search
USPC .......................... 514/89, 645; 564/300; 568/9
See application file for complete search history.

(56) References Cited

U.S. PATENT DOCUMENTS

2004/0024025 A1  2/2004  Kasid et al.
2007/0066572 A1*  3/2007  Balaraman et al. ............. 514/89

FOREIGN PATENT DOCUMENTS

| JP | 2004 262823 | 9/2004 |
| JP | 2004262823 | * 9/2004 |
| WO | WO 98/53835 | 12/1998 |
| WO | WO 00/00157 | 1/2000 |

OTHER PUBLICATIONS

Trnka et. al., Free Radical Biology and Medicine, 2008, Elsevier, vol. 44, pp. 1406-1419.*
Mravljak, J., et al., "Synthesis and Biological Evaluation of Spin-Labeled Alkylphospholipid Analogs," J. Med. Chem, 2005, 48, 6393-6399.
Chignell, Colin F., et al.: "Synthesis of Some Spin-Labeled Analogs of Drug Molecules", Journal of Medicinal Chemistry, 15(8), pp. 876-878, 1972.
Dessolin, Jean, et al.: "Selective Targeting of Synthetic Antioxidants to Mitochondria: Towards a Mitochondrial Medicine for Neurodegenerative Diseases?", European Journal of Pharmacology, 447(2-3), pp. 155-161, 2002.
Dhanasekaran, Anuradha, et al.: "Mitochondria Superoxide Dismutase Mimetic Inhibits Peroxide-Induced Oxidative Damage and Apoptosis: Role of Mitochondrial Superoxide", Free Radical Biology & Medicine, 39(5), pp. 567-583, 2005.
Hartsel, Scott C., et al.: "Time-Dependent Binding of Paramagnetic and Fluorescent Hydrophobic Ions to the Acetylcholine Receptor from Torpedo", Biochemistry, 26(12), pp. 3253-3260, 1987.
Ishii, K., et al.: "In Vitro Photodynamic Effects of Phthalocyaninatosilicon Covalently Linked to 2,2,6,6-Tetramethyl-1-Piperidinyloxy Radicals on Cancer Cells", Free Radical Biology and Medicine, 38(7), pp. 920-927, 2005.
Kubota, Jun, et al.: "Water-Soluble N-Oxyl Compounds-Mediated Electrooxidation of Alcohols in Water: A Prominent Access to a Totally Closed System", Tetrahedron Letters, 46(52), pp. 8975-8979, 2005.

* cited by examiner

*Primary Examiner* — Sreeni Padmanabhan
*Assistant Examiner* — Sarah Pihonak
(74) *Attorney, Agent, or Firm* — Nixon Peabody LLP

(57) ABSTRACT

The inventions disclosed include methods of treating cancers and related neoplasias, especially prostate cancer, with pharmaceutically acceptable salts comprising lipophilic cation moieties linked to nitroxide or linked to hydroxylamine anti-oxidant groups.

3 Claims, 8 Drawing Sheets

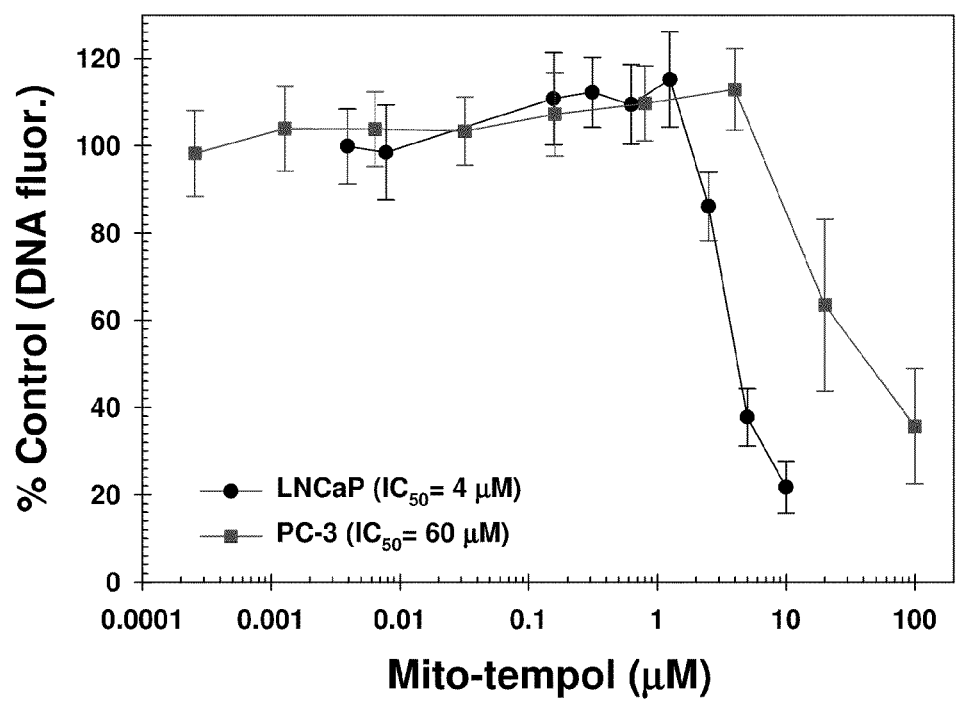
Figure 1. Inhibitory effect of MitoT on the growth of LNCaP (black line with filled black circles) and PC-3 (red line with filled red squares) cells, as determined by Hoechst dye-DNA fluorescence assays.

Figure 2. DCF fluorescence (green) and Hoechst dye-DNA fluorescence (blue) in LNCaP cells under elevated oxidative stress due to treatment with 1 nM of synthetic androgen analog (R1881).

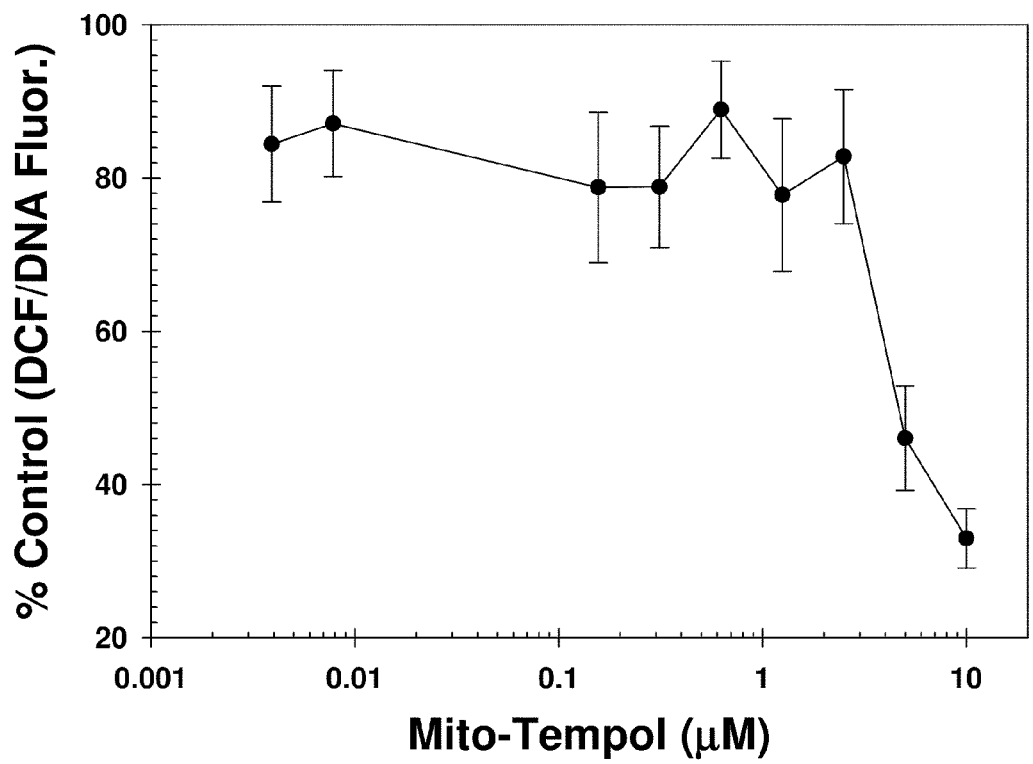
Figure 3. Inhibitory effect of MitoT on the oxidative stress level in LNCaP prostate tumor cells as determined by the ratio of DCF fluorescence/Hoechst dye-DNA fluorescence.

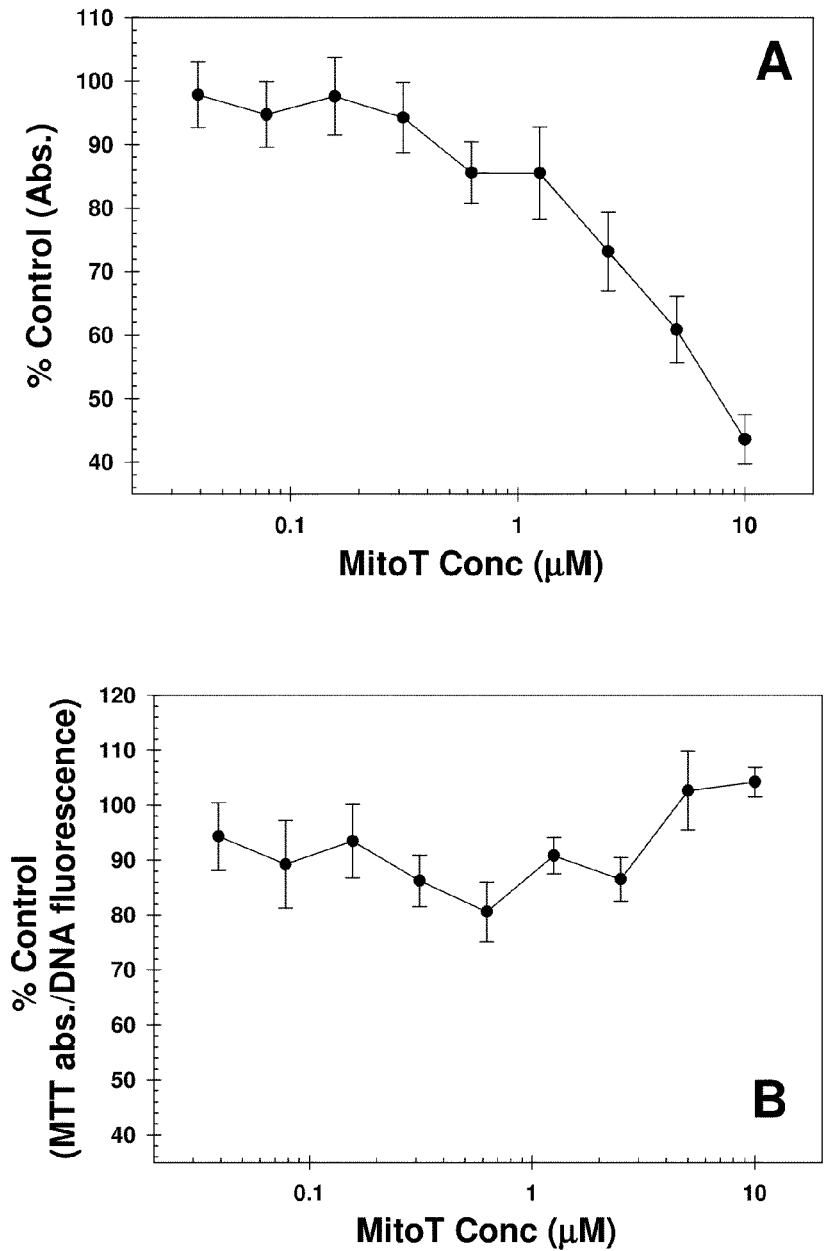

Figure 4. MitoT treatment reduces the ROS level and causes cell growth inhibition in LNCaP prostate cancer cells (A) Plot of % control of MTT absorbance at increasing MitoT concentration shows MitoT absorbs mitochondrial electrons. (B) Plot of the ratio of % of control cell MTT absorbance/DNA fluorescence shows that the decrease in MTT oxidation is positively correlated to cell growth arrest.

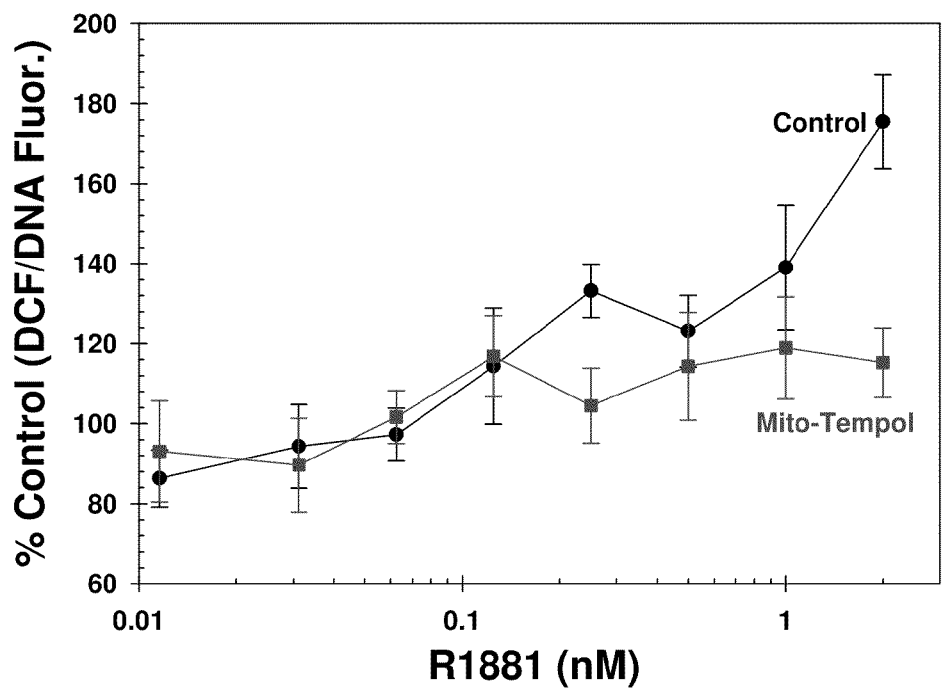
Figure 5. Androgen (R1881) treatment induced oxidative stress increase in LNCaP human prostate cancer cells, as determined by the ratio of DCF fluorescence/DNA fluorescence is strongly inhibited by pretreatment of the tumor cells with 1 μM Mito-T.

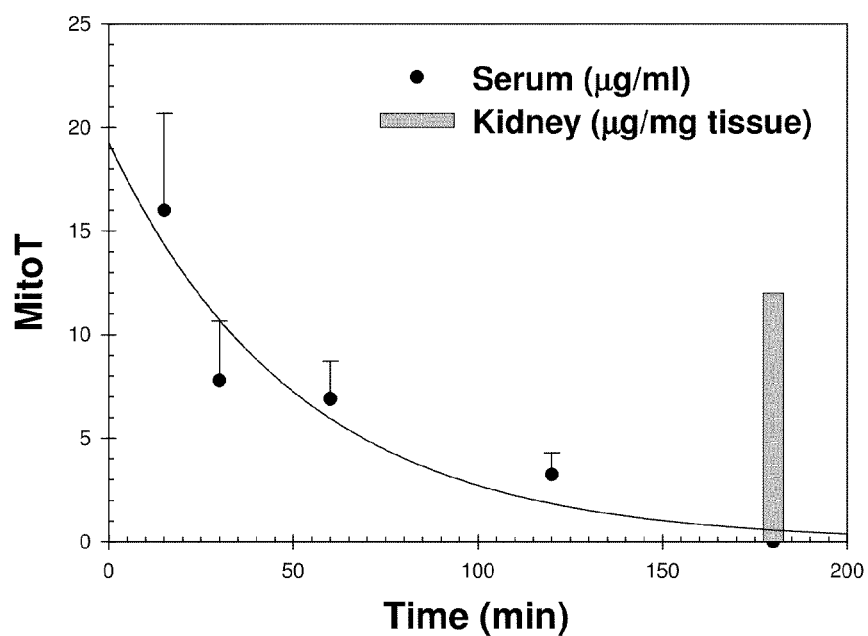
Figure 6. Pharamacokinetics of MitoT in serum and in kidney tissues of white mice given one i.p. injection of MitoT (5 mg/kg) showing serum clearance and tissue accumulation of the drug with time.

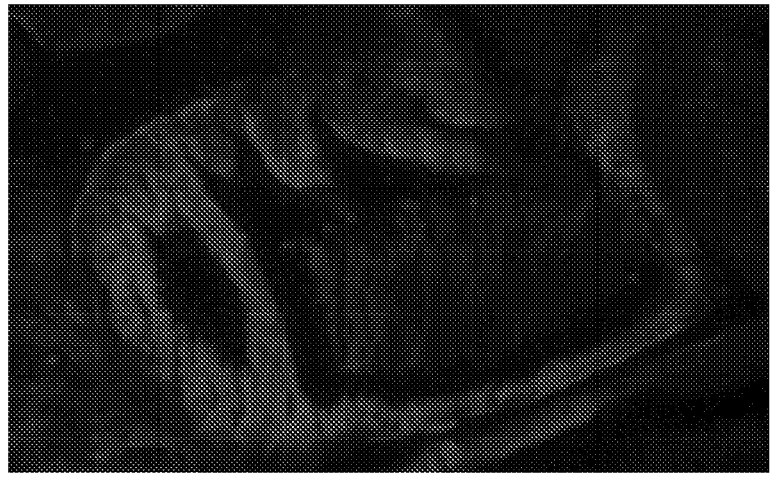
A
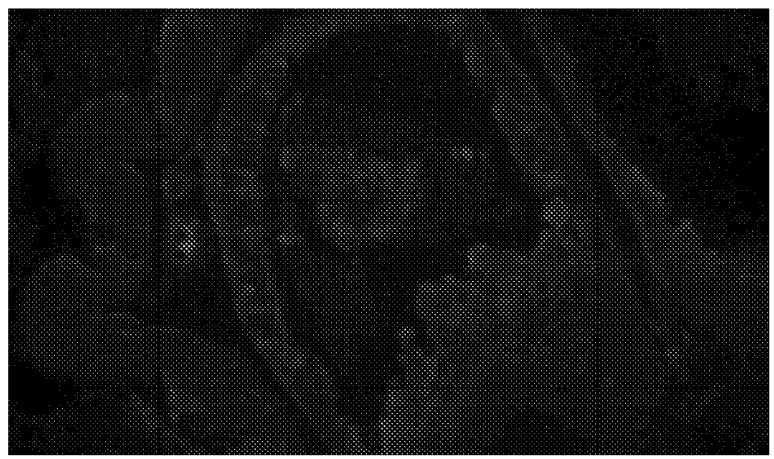
B
Figure 7. Hydroethidine dye fluorescence due to ROS oxidation in kidney tissue of (A) untreated mice (0 mg/kg Mito T for 3 hours) and (B) mice treated with 5 mg/kg MitoT for 3 hours.

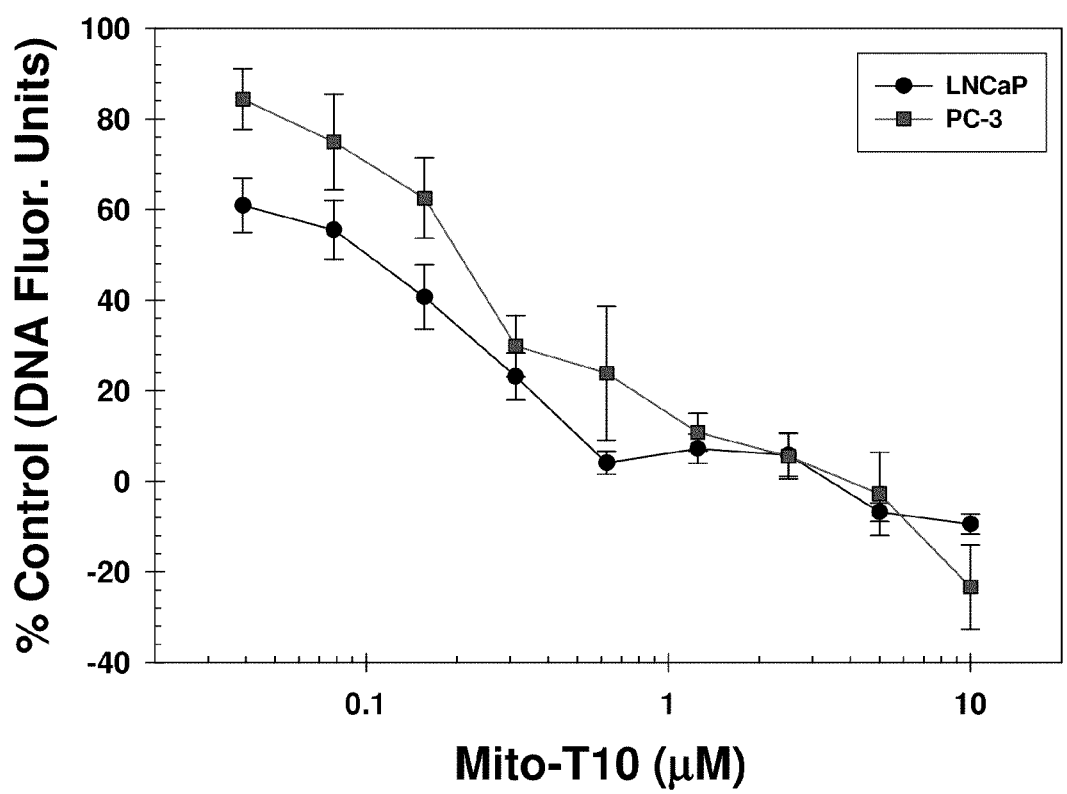
Figure 8. Inhibitory effect of MitoT-10 on the growth of LNCaP and PC-3 human prostate cancer cells, as determined by Hoechst dye-DNA fluorescence assays.

MITOCHONDRIA TARGETED CATIONIC ANTI-OXIDANT COMPOUNDS FOR PREVENTION, THERAPY OR TREATMENT OF HYPER-PROLIFERATIVE DISEASE, NEOPLASIAS AND CANCERS

GOVERNMENT SUPPORT

This invention was made with government support under Grant No. 63119 awarded by NIH/NHLBI. The government has certain rights in the invention.

PRIORITY STATEMENT

This application claims benefit of priority as applicable under 35 U.S.C. §120 as a continuation of PCT/US2008/056035, filed Mar. 6, 2008, which claims benefit under 35 U.S.C. §119(e) of U.S. Provisional Application No. 60/905,237, filed Mar. 6, 2007.

FIELD OF THE INVENTION

The inventions described herein relate to the treatment of various forms of cancer, or related neoplasias, with compounds that comprise one or more quaternary cationic moieties chemically linked to one or more anti-oxidant moieties comprising nitroxide or amine oxide moieties.

BACKGROUND

Oxidative stress has been known to contribute to a variety of human degenerative diseases associated with aging, such as Parkinson's disease and Alzheimer's disease, as well as to Huntington's Chorea, diabetes and Friedreich's Ataxia (Allen, S., et al., J. Biol. Chem. 278:6371-6383, 2003; Hirai, K., et al., J. Neurosci. 21:3017-3023, 2001) and to non-specific cellular damage that accumulates with aging.

Mitochondria are the intracellular organelles primarily responsible for energy metabolism, and are also the major source of the free radicals and reactive oxygen species ("ROS", such as hydrogen peroxide and the superoxide radical anion ($O_2^-$)) that cause oxidative stress and/or damage inside most cells (Murphy M P, Smith R A., Ann. Rev Pharmacol Toxicol. 2006 Oct. 2; Epub ahead of print). Mitochondria are equipped to detoxify hydrogen peroxide due to the presence of antioxidant enzymes (peroxiredoxins, thioredoxins, and GSH-dependent peroxidases (Chang, T. S., J. Biol. Chem. 279, 41975-41984, 2004). Typically, mitochondrial superoxide ($O_2^-$, the radical anion produced by one electron reduction of $O_2$) is dismutated according to the stoichiometry shown below, by manganese superoxide dismutase (MnSOD) that is localized within the mitochondrial matrix.

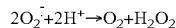

$2O_2^- + 2H^+ \rightarrow O_2 + H_2O_2$

However, when cellular ROS production exceeds the cell's detoxification capacity, oxidative damage can occur. This damage disrupts mitochondrial function and oxidative phosphorylation and leads to significant cellular damage to mitochondrial, cytoplasmic or nuclear cellular proteins, DNA, RNA and phospholipids and thus induces cell damage, death and/or disease. Superoxide can also react with nitric oxide at a diffusion-controlled reaction rate, forming a highly potent oxidant and peroxynitrite that can modify proteins and DNA through oxidation and nitration reactions (Beckman, J. S., et al., Nature 364, 584, 1993). In addition to these damaging and pathological roles, ROS also act as a redox signaling molecule(s) and promotes cell proliferation, DNA damage repair errors and mutation leading to inflammatory hyper-proliferation, neoplasia and malignancy (see Michikawa et. al., "Aging-dependent large accumulation of point mutations in the human mtDNA control region for replication." Science. 1999 Oct. 22; 286(5440):774-9).

Naturally occurring exogenous and endogenous tissue reactive oxygen species (ROS) are known to play a major role in prostate, colorectal, lymphoma and pancreatic carcinogenesis (De Marzo et al, J Cell Biochem. 2004 Feb. 15; 91(3): 459-77; Reliene R, Schiestl R H. Antioxidants suppress lymphoma and increase longevity in ATM-deficient mice. J Nutr. 2007 January; 137(1):229S-32S). ROS alters the activity of thiol-dependent enzymes, changes the cellular redox balance and covalently modifies proteins and modifies and mutagenizes DNA (Sikka S C., Curr Med Chem. 2001 June; 8(7):851-62. Kamat A M, Lamm D L. W V Med J. 2000; 96: 449-54). It has also been shown that increased lipid peroxidation and production of high levels of unregulated ROS in men with high fat diets is one of the major reasons for the higher incidence of prostate cancer in industrialized nations, as compared to that in developing countries (Dargel, R., Exp Toxic Pathol 1992, 44:169-181). In recent years, direct experimental evidence has linked increased ROS levels with the corresponding increase in mutations and tumor development in various tissues, including in the pancreas and the prostate organs (Oberley et. al., The Prostate, 2000: 44: 144-155). For example, Oberley and his colleagues monitored oxidative stress induced enzymes and oxidative damage to DNA bases of malignant and normal human prostate tissues. Malignant prostate tumor tissues showed significantly higher oxidative stress and ROS-induced DNA modifications as compared to normal prostate tissues. Ho and her coworkers (Tam et al., Prostate. 2006 Jan. 1; 66(1):57-69) demonstrated the presence of high oxidative stress induced DNA modifications in the pre-neoplastic lesions occurring in the well studied TRAM P (Transgenic Adenocarcinoma of Mouse Prostate) and Noble rat (Tam et al., Sex Hormones induce direct epithelial and inflammation-mediated oxidative/nitrosative stress that favors prostatic carcinogenesis in the Noble rat. Am. J. Pathol. 2007 October 117(4);1334-41, Epub. 2007 Aug. 23) prostate cancer mouse model of human prostate cancer.

Hence, unregulated mitochondrial ROS production, the resulting oxidative cellular damage-induced-carcinogenesis represent unsolved problems in the art, and present a compelling target for pharmacological drug interventions with pharmaceutical anti-superoxide small molecule drug formulations.

To prevent the cellular damage caused by oxidative stress a number of prior art anti-oxidant therapies have been developed for treating various diseases resulting from oxidative stress. However, most of those inventions are not targeted to other organelles within cells or to the mitochondria and are therefore less than optimally effective.

In recent years, there has been interest in mitochondria-targeting technologies (see Murphy M P. "Selective targeting of bioactive compounds to mitochondria." Trends Biotechnol. 1997 August; 15(8):326-30). In these approaches, "warhead" groups are covalently coupled via linker groups to a bulky and/or lipophilic cationic moiety such as a quaternary ammonium or phosphonium cationic moiety. These compounds are initially absorbed and accumulate in the cytoplasmic region of cells in response to the negative plasma membrane potential of 30-60 mV (3). Additionally, within a few minutes after drug treatment, the lipophilic cations with a positive 30-60 mV potential permeate through the mitochondrion's lipid layers and selectively accumulate within mitochondria due to the larger mitochondrial membrane potential of 150-170 mV; (negative inside).

Mitochondria-targeted compounds in this class of agents are shown below and include a mitochondria-directed ubiquinone (MitoQ) reported by Murphy and coworkers (U.S. Pat. Nos. 6,331,532 and 7,232,809, and EP Patent 1 047 701 B1, all of which are herein incorporated by reference in their entirety).

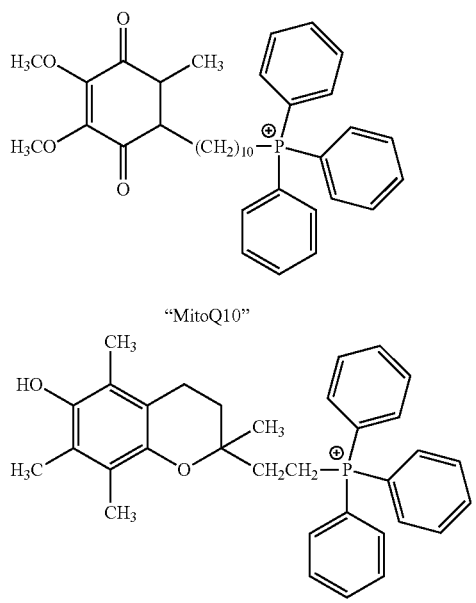

MitoQ has shown promise in the treatment of only some, but not all, oxidative stress induced diseases. MitoQ is currently undergoing Phase II clinical trials for the treatment of Parkinson's disease, but it has relatively minor activity against other oxidative stress-induced neurodegenerative diseases such as Amyotrophic Lateral Sclerosis (ALS or Lou Gehrig's Disease). This class of compounds is also disclosed in U.S. Published Application No. U.S. 2008/0032940, herein incorporated by reference in its entirety, in the context of methods for treating cancer.

Other classes of mitochondria-targeted compounds include mitochondria-targeted nitroxides, which have been used in method for treating neurodegenerative disorders (see U.S. Published Application No. 2007/0066572, herein incorporated by reference in its entirety) and mitochondria-targeted antioxidants, which have been used in methods for treating cancer (see U.S. application Ser. No. 11/834,799, entitled "Methods for Reducing Anthracycline-Induced Toxicity," filed Aug. 7, 2007, herein incorporated by reference in its entirety).

Accordingly, there remains a need for mitochondrially targeted anti-inflammatory, anti-proliferative anti-cancer agents with improved properties and/or toxicity profiles and it is towards the provision of such anti-oxidants, which may be targeted to mitochondria that the various inventions disclosed and described below are directed.

SUMMARY

One aspect of the disclosure relates to methods for treating or inhibiting the occurrence, recurrence, progression or metastasis, of a cancer or a neoplastic or hyper-proliferative precursor thereof, consisting of administering to a mammal diagnosed as having a cancer or precursor neoplasia or hyperproliferative disorder thereof, in an amount effective to treat the cancer or inhibit the occurrence recurrence, progression, or metastasis of the cancer or precursor hyperplasia or neoplasia thereof, a pharmaceutically acceptable salt comprising one or more cations having the formula:

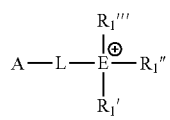

wherein
a) A is an antioxidant moiety comprising one or more nitroxide or hydroxyl amine moieties, or a pro-drug thereof, having from three to 16 carbon atoms,
b) L is an organic linking moiety comprising 4 to 30 carbon atoms,
c) E is a nitrogen or phosphorus atom,
d) $R_1'$, $R_1''$, and $R_1'''$ are each independently selected organic moieties comprising between 1 and 12 carbon atoms,
wherein E, $R_1'$, $R_1''$, and $R_1'''$ together form a quaternary ammonium or phosphonium cation;
and wherein the salt further comprises one or more $X^{m-}$ pharmaceutically acceptable anions, where m is an integer from 1 to 4, in sufficient quantities to form the pharmaceutically acceptable salt.

A related aspect of the disclosure relates to a method for treating, regulating or inhibiting the prostate's inflammation, hyperplasia or enlargement and the occurrence, recurrence, progression or metastasis of prostate cancer, consisting of administering to a mammal diagnosed as having prostate disease or cancer or precursor neoplasia thereof, in an amount effective to treat the cancer or modulate the inflammation, hyperplasia, or enlargement of the prostate or the occurrence, recurrence, progression, or metastasis of prostate cancer or precursor neoplasia thereof, with one or more pharmaceutically acceptable salts having one or more cations having the formula

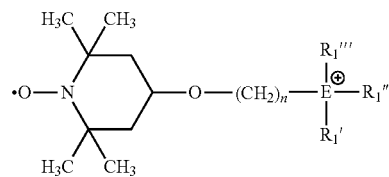

wherein
a) E is a nitrogen or phosphorus atom,
b) $R_1'$, $R_1''$, and $R_1'''$ are each independently selected organic moieties comprising between 1 and 12 carbon atoms,
c) n is an integer between 8 and 12, and
d) $R_1'$, $R_1''$, and $R_1'''$ are each independently selected organic moieties comprising between 1 and 12 carbon atoms,
wherein E, $R_1'$, $R_1''$, and $R_1'''$ together form a quaternary ammonium or phosphonium cation;
wherein the salt further comprises one or more pharmaceutically acceptable anions $X^{m-}$, wherein m is an integer from 1 to 4, in sufficient amount to form the pharmaceutically acceptable salt.

In other related aspects, the inventions described and disclosed herein relate to salts comprising one or more cations having the formula:

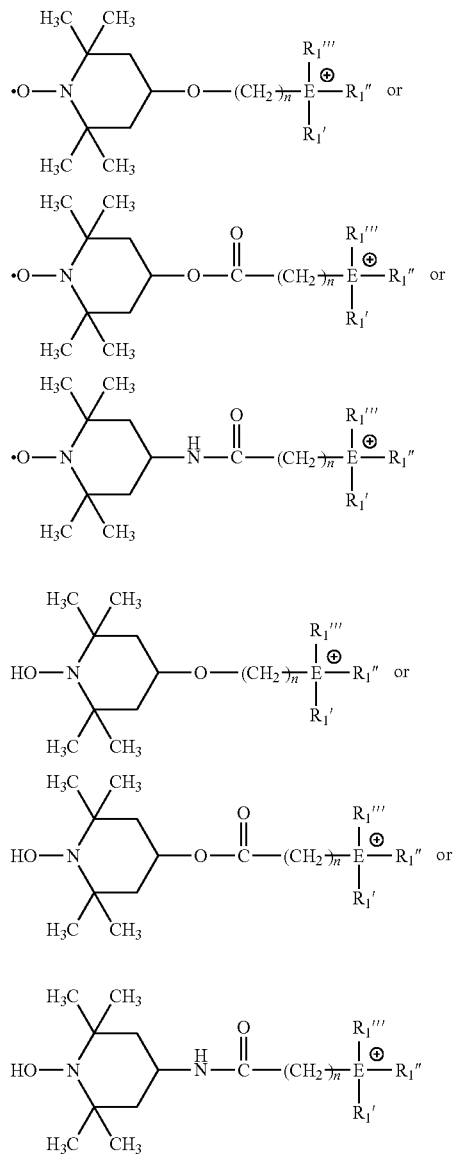

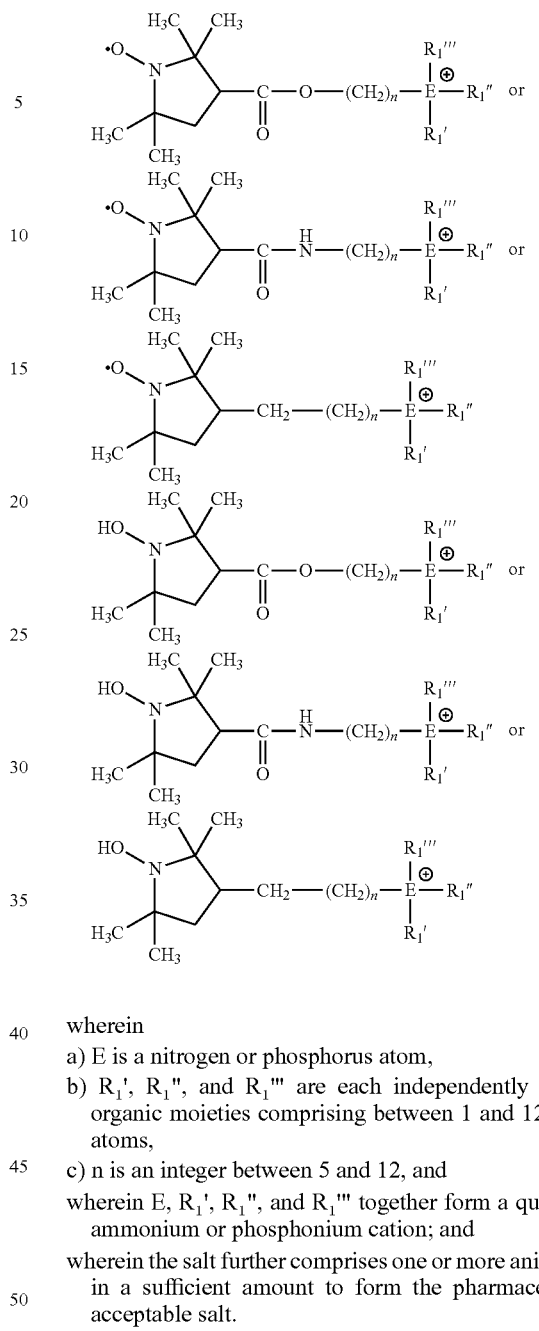

wherein
a) E is a nitrogen or phosphorus atom,
b) $R_1'$, $R_1''$, and $R_1'''$ are each independently selected organic moieties comprising between 1 and 12 carbon atoms,
c) n is an integer between 5 and 12, and
wherein E, $R_1'$, $R_1''$, and $R_1'''$ together form a quaternary ammonium or phosphonium cation; and
wherein the salt further comprises is one or more pharmaceutically acceptable anions $X^{m-}$, wherein m is an integer from 1 to 4, in sufficient amount to form the pharmaceutically acceptable salt.

Another aspect of the disclosure relates to salts comprising one or more cations having the formula:

wherein
a) E is a nitrogen or phosphorus atom,
b) $R_1'$, $R_1''$, and $R_1'''$ are each independently selected organic moieties comprising between 1 and 12 carbon atoms,
c) n is an integer between 5 and 12, and
wherein E, $R_1'$, $R_1''$, and $R_1'''$ together form a quaternary ammonium or phosphonium cation; and
wherein the salt further comprises one or more anions $X^{m-}$ in a sufficient amount to form the pharmaceutically acceptable salt.

It is understood that the examples and embodiments described above are for illustrative purposes only and that various modifications or changes in light thereof will be suggested to persons skilled in the art and are to be included within the spirit and purview of this application and scope of the appended claims.

Additional aspects of the inventions and advantages thereof will be set forth in part in the description which follows and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below Like numbers represent the same elements throughout the figures.

FIG. 1 shows the inhibitory effect of varying concentrations of MitoT on the proliferation and growth of human prostate tumor LNCaP and PC-3 cells, as determined by Hoechst dye-DNA fluorescence assays.

FIG. 2 shows a microscopic picture of DCF fluorescence (green) and Hoechst dye-DNA fluorescence (blue) in human prostate tumor LNCaP cells, which have been placed under high oxidative stress due to treatment of the cells with a 1 nM solution of the synthetic androgen analog, R1881.

FIG. 3 shows the inhibitory effect of treatment with varying concentrations of MitoT on the oxidative stress levels in LNCaP human prostate tumor cells, as determined by the ratio of DCF fluorescence/Hoechst dye-DNA fluorescence.

FIG. 4 shows that MitoT treatment at sufficient concentrations reduces the ROS level and causes inhibition of cell growth and proliferation in LNCaP human prostate cancer cells (A) Plot of % control of MTT absorbance at increasing MitoT concentration shows MitoT absorbs mitochondrial electrons. (B) Plot of the ratio of % of control cell MTT absorbance/DNA fluorescence shows that the decrease in MTT oxidation is related to cell growth arrest.

FIG. 5 shows that synthetic androgen (R1881) treatment-induced oxidative stress in LNCaP human prostate cancer cells, as determined by the ratio of DCF fluorescence/DNA fluorescence, is strongly inhibited by pre-treatment of the cells with 1 µM MitoT.

FIG. 6 shows the pharamacokinetics of MitoT absorption in serum and in kidney tissues of white mice given one intraperitoneal (i.p.) injection of MitoT (5 mg/kg) showing serum clearance and tissue accumulation of the drug with the passage of time.

FIG. 7 shows pictorial microscopic evidence of Hydroethidine dye fluorescence due to ROS oxidation in kidney tissue of (A) untreated mice and (B) mice treated with 5 mg/kg MitoT for 3 hours.

FIG. 8 shows the inhibitory effect of varying concentrations of MitoT-10 on the growth and proliferation of LNCaP and PC-3 human prostate cancer cells, as determined by Hoechst dye-DNA fluorescence assays

DETAILED DESCRIPTION

Before the disclosure is described in detail, it is understood that scope of this disclosure is not limited to the particular methodology, protocols, cell lines, and reagents described, as these may vary. It is also to be understood that the terminology used herein is for the purpose of describing particular embodiments only and is not intended to limit the scope of the disclosure, which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

Often, ranges are expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or can not be substituted and that the description includes both unsubstituted lower alkyl and lower alkyl where there is substitution.

A cell can be in vitro. Alternatively, a cell can be in vivo and can be found in a subject. A "cell" can be a cell from any organism including, but not limited to, a bacterium or a mammalian cell or a tumor cell.

As used throughout, by a "subject" is meant an individual. Thus, the "subject" can include domesticated animals, such as cats, dogs, etc., livestock (e.g., cattle, horses, pigs, sheep, goats, rabbits, etc.), laboratory animals (e.g., mouse, rabbit, rat, guinea pig, ferret, mink, etc.) and birds. In one aspect, the subject is a higher mammal such as a primate or a human.

In one aspect, the compounds described herein can be administered to a subject comprising a human or an animal including, but not limited to, a murine, canine, feline, equine, bovine, porcine, caprine or ovine species and the like, that is in need of alleviation or amelioration from a recognized medical condition.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

The term "moiety" defines a carbon containing residue, i.e. a moiety comprising at least one carbon atom, and includes but is not limited to, the carbon-containing groups defined hereinabove. Organic moieties can contain various heteroatoms, or be bonded to another molecule through a heteroatom, including oxygen, nitrogen, sulfur, phosphorus, or the like. Examples of organic moieties include but are not limited alkyl or substituted alkyls, alkoxy or substituted alkoxy, mono or di-substituted amino, amide groups, etc. Organic moieties can preferably comprise 1 to 21 carbon atoms, 1 to 18 carbon atoms, 1 to 15, carbon atoms, 1 to 12 carbon atoms, 1 to 8 carbon atoms, or 1 to 4 carbon atoms.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

The term "alkyl" denotes a moiety containing a saturated, straight or branched hydrocarbon residue having from 1 to 18 carbons, or preferably 4 to 14 carbons, 5 to 13 carbons, or 6 to 10 carbons. An alkyl is structurally similar to a non-cyclic alkane compound modified by the removal of one hydrogen from the non-cyclic alkane and the substitution, therefore, with a non-hydrogen group or moiety. Alkyl moieties can be branched or unbranched. Lower alkyl moieties have 1 to 4 carbon atoms. Examples of alkyl moieties include methyl, ethyl, n-propyl, iso-propyl, n-butyl, sec-butyl, t-butyl, amyl, t-amyl, n-pentyl and the like.

The term "substituted alkyl" denotes an alkyl moiety analogous to the above definition that is substituted with one or more organic or inorganic substituent moieties. In some embodiments, 1 or 2 organic or inorganic substituent moieties are employed. In some embodiments, each organic substituent moiety comprises between 1 and 4, or between 5 and 8 carbon atoms. Suitable organic and inorganic substituent moieties include, but are not limited to, hydroxyl, halogens, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, heteroaryl, substituted heteroaryl, aryl or substituted aryl. When more than one substituent group is present then they can be the same or different.

Abbreviations used herein include:

The term "alkoxy" as used herein denotes a moiety alkyl, defined above, attached directly to a oxygen to form an ether residue. Examples include methoxy, ethoxy, n-propoxy, iso-propoxy, n-butoxy, t-butoxy, iso-butoxy and the like.

The term "substituted alkoxy" denotes a alkoxy moiety of the above definition that is substituted with one or more groups, but preferably one or two substituent groups including hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy or haloalkoxy. When more than one group is present then they can be the same or different.

The term "mono-substituted amino" denotes an amino ($-NH_2$) group substituted with one group selected from alkyl, substituted alkyl or arylalkyl wherein the terms have the same definitions found throughout.

The term "di-substituted amino" denotes an amino substituted with two moieties that can be same or different selected from aryl, substituted aryl, alkyl, substituted alkyl or arylalkyl wherein the terms have the same definitions found throughout. Some examples include dimethylamino, methylethylamino, diethylamino and the like.

The term "haloalkyl" denotes a alkyl moiety, defined above, substituted with one or more halogens, preferably fluorine, such as a trifluoromethyl, pentafluoroethyl and the like.

The term "haloalkoxy" denotes a haloalkyl, as defined above, that is directly attached to an oxygen to form a halogenated ether residue, including trifluoromethoxy, pentafluoroethoxy and the like.

The term "acyl" denotes a moiety of the formula $-C(O)-R$ that comprises a carbonyl ($C=O$) group, wherein the R moiety is an organic moiety having a carbon atom bonded to the carbonyl group. Acyl moieties contain 1 to 8 or 1 to 4 carbon atoms. Examples of acyl moieties include but are not limited to formyl, acetyl, propionyl, butanoyl, iso-butanoyl, pentanoyl, hexanoyl, heptanoyl, benzoyl and like moieties.

The term "acyloxy" denotes a moiety containing 1 to 8 carbons of an acyl group defined above directly attached to an oxygen such as acetyloxy, propionyloxy, butanoyloxy, iso-butanoyloxy, benzoyloxy and the like.

The term "aryl" denotes an unsaturated and conjugated aromatic ring moiety containing 6 to 18 ring carbons, or preferably 6 to 12 ring carbons. Many aryl moieties have at least one six-membered aromatic "benzene" moiety therein. Examples of such aryl moieties include phenyl and naphthyl.

The term "substituted aryl" denotes an aryl ring moiety as defined above that is substituted with or fused to one or more organic or inorganic substituent moieties, which include but are not limited to a halogen, alkyl, substituted alkyl, haloalky, hydroxyl, cycloalkyl, substituted cycloalkyl, cycloalkenyl, substituted cycloalkenyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy or haloalkoxy, aryl, substituted aryl, heteroaryl, heterocyclic ring, substituted heterocyclic ring moiety, wherein the terms are defined herein. Substituted aryl moieties can have one, two, three, four, five, or more substituent moieties. The substituent moieties can be not be of unlimited size or molecular weight, and each organic moiety can comprise 15 or fewer, 10 or fewer, or 4 or fewer carbon atoms unless otherwise expressly contemplated by the claims The term "heteroaryl" denotes an aryl ring moiety as defined above, wherein at least one of the carbons of the aromatic ring has been replaced with a heteroatom, which include but are not limited to nitrogen, oxygen, and sulfur atoms. Heteroaryl moieties include 6 membered aromatic ring moieties, and can also comprise 5 or 7 membered aromatic rings, or bicyclic or polycyclic heteroaromatic rings as well. Examples of heteroaryl moieties include pyridyl, bipyridyl, furanyl, and thiofuranyl residues. It is to be understood that the heteroaryl moieties can optionally be substituted with one or more organic or inorganic substituent moieties bound to the carbon atoms of the heteroaromatic rings, as described hereinabove for substituted aryl moieties. Substituted heteroaryl moieties can have one, two, three, four, five, or more substituent organic or inorganic moieties, in a manner analogous to the substituted aryl moieties defined herein. The substituent moieties cannot be of unlimited size or molecular weight, and each organic substituent moiety can comprise 15 or fewer, 10 or fewer, or four or fewer carbon atoms unless otherwise expressly contemplated by the claims.

The term "halo," "halide," or "halogen" refers to a fluoro, chloro, bromo or iodo atom or ion.

The term "heterocycle" or "heterocyclic", as used in the specification and concluding claims, refers to a moiety having a closed ring structure comprising 3 to 10 ring atoms, in which at least one of the atoms in the ring is an element other than carbon, such as, for example, nitrogen, sulfur, oxygen, silicon, phosphorus, or the like. Heterocyclic compounds having rings with 5, 6, or 7 members are common, and the ring can be saturated, or partially or completely unsaturated. The heterocyclic compound can be monocyclic, bicyclic, or polycyclic. Examples of heterocyclic compounds include but are not limited to pyridine, piperidine, thiophene, furan, tetrahydrofuran, and the like. The term "substituted heterocyclic" refers to a heterocyclic moiety as defined above having one or more organic or inorganic substituent moieties bonded to one of the ring atoms.

The term "carboxy", as used in the specification and concluding claims, refers to the —C(O)OH moiety that is characteristic of carboxylic acids. The hydrogen of the carboxy moieties is often acidic and (depending on the pH) often partially or completely dissociates, to form an acid H+ ion and a carboxylate anion (—$CO_2^-$), wherein the carboxylate anion is also sometimes referred to as a "carboxy" moiety.

It is understood that when a chiral atom is present in a compound disclosed herein, both separated enantiomers, racemic mixtures and mixtures of enantiomeric excess are within the scope of the invention. Separation of such mixtures may be done using techniques known in the art. As defined herein, a racemic mixture is an equal ratio of each of the enantiomers, whereas an enantiomeric excess is when the percent of one enantiomer is greater than the other enantiomer, all percentages are within the scope of the invention. Furthermore, when more than one chiral atom is present in a compound, then the enantiomers, racemic mixtures, mixtures of enantiomeric excess and diastereomic mixtures are within the scope of the invention.

II. The Inventions

Compounds Employed in the Inventions

The compounds described below are salts, and can be used for the treatment of various diseases as disclosed elsewhere herein. As will be appreciated by those of ordinary skill in the art, the salts comprise a mixture of cations and anions whose total number of positive and negative charges are electrically balanced. More particularly, however, the salts disclosed herein have one or more cations having the Formula (I) illustrated below

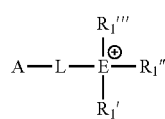

wherein
a) A is an antioxidant moiety comprising one or more nitroxide or hydroxylamine moieties, or a prodrug thereof,
b) L is an organic linking moiety,
c) E is a nitrogen or phosphorus atom,
d) $R_1'$, $R_1''$, and $R_1'''$ are each independently selected from organic moieties comprising between 1 and 12 carbon atoms,
wherein E, $R_1'$, $R_1''$, and $R_1'''$ together form a quaternary ammonium or phosphonium cation; and
wherein the salt further comprises is one or more pharmaceutically acceptable anions $X^{m-}$, wherein m is an integer from 1 to 4, in sufficient amount to form the pharmaceutically acceptable salt.

The various genera, subgenera, and species of the compounds of Formula (I) share at least the features disclosed above, and have related functions and utilities, but can differ in specific structural features, as described below.

The Antioxidant "A" Moieties

The compounds of the invention all comprise at least one antioxidant moiety "A" which comprises at least one or more nitroxide radial or hydroxyl amine moieties bonded therein or thereto.

Nitroxides and relevant hydroxylamines have the chemical structures shown below:

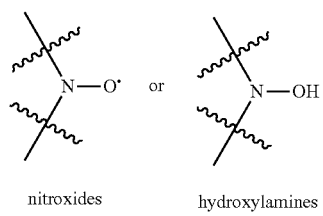

nitroxides        hydroxylamines

It is well known, as explained above, that superoxide anion is formed in relatively large concentrations in the mitochondria of cells, and that excess concentrations of superoxide are deleterious to the mitochondria and other parts of the cell. It is well known in the art that nitroxides and/or hydroxylamines can function to catalyze the dismutation of superoxide anion in the fashion illustrated below.

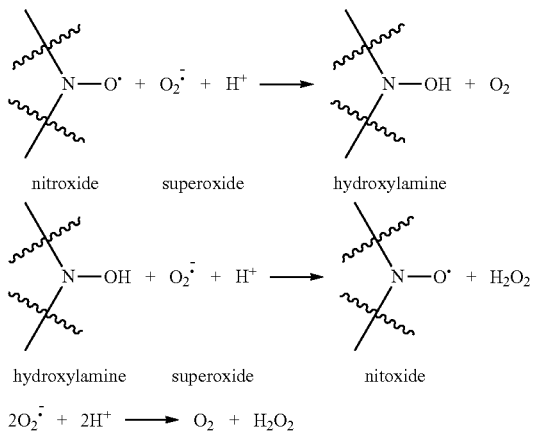

Accordingly, the "A" moieties of the salts described herein, which comprise one or more nitroxide or hydroxyl amine moieties, can catalyze the dismutation of superoxide radical anions in the cell, to form hydrogen peroxide which can be dealt with by enzymes in the cell, and therefore serve to function as "anti-oxidants." The nitroxide or hydroxylamine moieties are part of a larger A moiety, which in many embodiments can comprise between 4 and 30 carbon atoms, or, 6 to 24 carbon atoms, or 7 to 18 carbon atoms, or from 8 to 12 carbon atoms.

In some embodiments, the A moieties have 5 or 6-member rings containing a nitroxide free radical therein having the formulas:

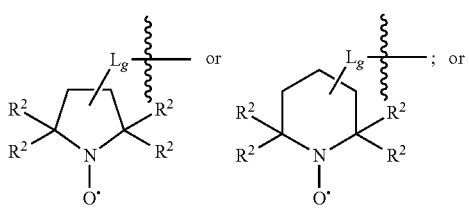

5 and 6-member rings containing a hydroxyl amine moiety having the formula:

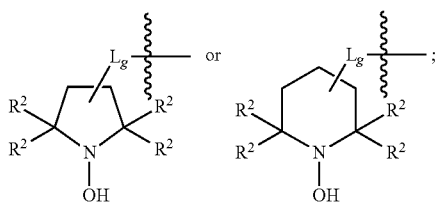

wherein the R² moieties are organic substitutent moieties. In some embodiments, the R² moieties can be $C_1$-$C_4$ alkyls, aryls, alkoxides, and the like. In some embodiments, the R² moieties can be $C_1$-$C_4$ linear or branched alkyl, for example, methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$).

In many embodiments, the R² moieties are all methyl groups as shown below, which are [2,2,5,5-tetramethylpyrrolidinyloxy] free radical having the formula:

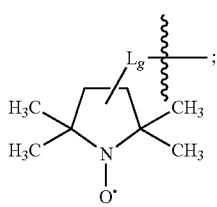

Similar A moieties having corresponding hydroxylamine moieties are 2,2,5,5-tetramethylpyrrolidin-1-ols having the formula:

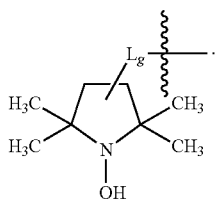

Such compounds comprising the five membered nitroxide or hydroxyl amine moieties incorporated into such five-membered heterocycles are often referred to in the art as "Proxyl" derivatives.

In other embodiments, the "A" moieties are [2,2,6,6-tetramethylpiperidinyloxy] free radical moieties the formula:

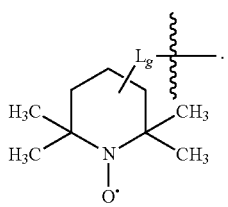

or 2,2,6,6-tetramethylpiperidin-1-ol moieties having the formula:

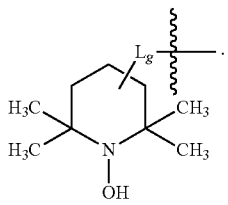

Such compounds comprising a nitroxide or hydroxyl amine moieties incorporated into such six-membered heterocycles are often referred to in the art as "Tempol" derivatives.

In the Proxyl or Tempol analogs shown above, $L_g$ can be any of a variety of moieties that form a bond to the "L$^s$" linking group. In many embodiments, $L_g$ can be one of the following moieties: —O—, —CH₂—; —CH₂—O—, —CH₂—NH—, —NR³—, —NR³C(O)—; —C(O)NR³—, —C(O)O—, —C(O)—, —OC(O)—, —NHC(O)NH—, or —NH(=NH)NH—, wherein R³ is hydrogen or a linear or branched $C_1$-$C_4$ alkyl, for example, methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$).

In some embodiments, the $L_g$ moieties taken together with nitroxide free radical moieties can provide "Tempol" analog moieties having the formula:

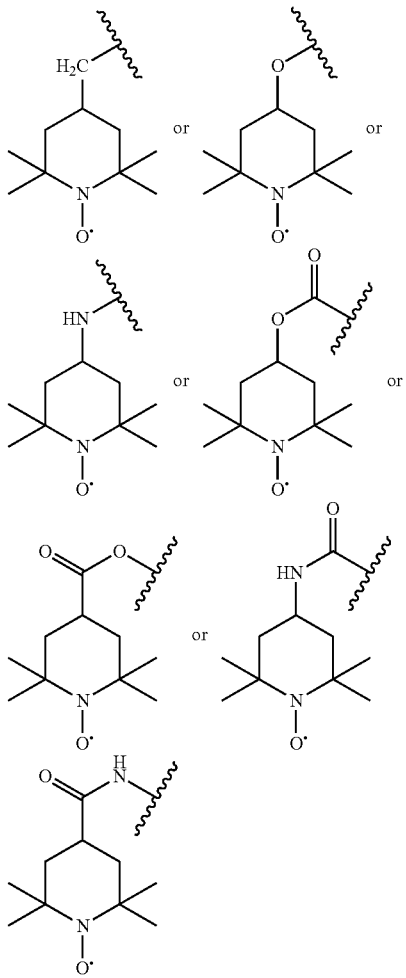

or any of the similar hydroxyl amine moieties having the formulas;
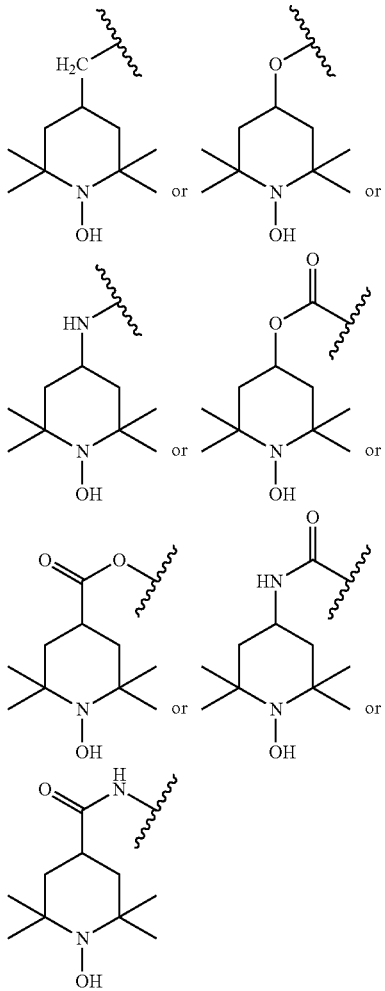
In some embodiments, the $L_g$ moieties taken together with nitroxide free radical moieties can provide "Proxyl" analog moieties having the formula:
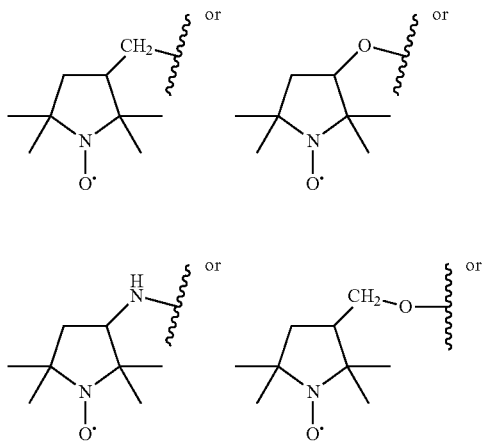
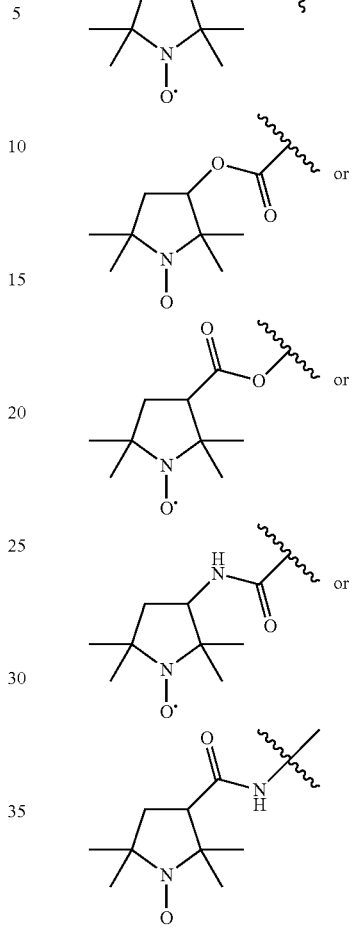
or any of the similar hydroxyl amine moieties having the formulas:
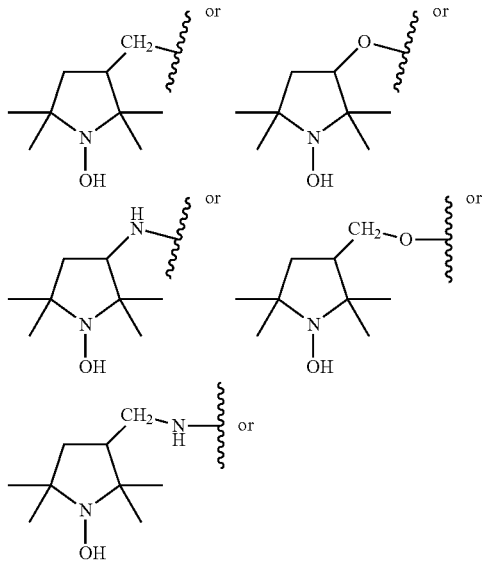

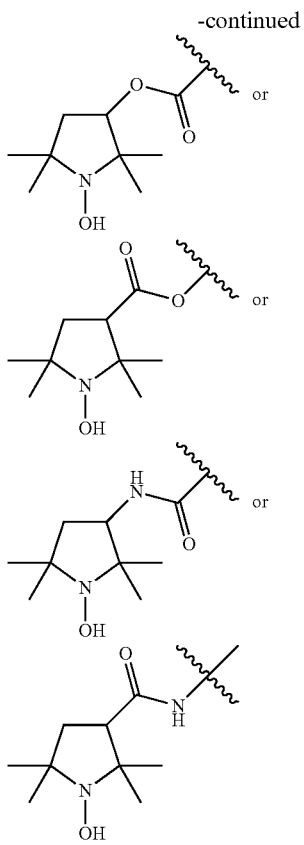 or

L moieties serve to connect the quaternary ammonium and/or phosphonium salt moieties with the A moieties. L moieties can comprise a polyalkylene chain having 5 to 30 carbon chain atoms, wherein any one or more of the hydrogens bonded to said carbon chain atoms can be optionally substituted with one or two independently selected hydroxyl, halogen, amino, methylamino, dimethylamino, or $C_1$-$C_4$ organic moieties selected from alkyl, hydroxyalkyl, alkoxy, alkoxylalkyl, carboxy, or carboxyalkyl moieties.

The Ammonium or Phosphonium Cationic Moieties

The compounds useful for the methods of the disclosure comprise one or more cationic moieties. The cationic moieties carry a positive charge, which, while not being bound by theory, is believed to cause the desirable selective accumulation of the resultant compounds in the mitochondria, because of the large mitochondrial membrane potential of 150-170 mV, and the resulting electrostatic attractions. Again, while not being bound by theory, it has been found that the selective accumulation of the cationic salts disclosed herein is also improved if the cationic moieties comprise relatively large and/or lipophilic organic substitutent moieties, so that the resulting cationic group is relatively lipophilic when considered as a whole. One of ordinary skill in the art will recognize that many relatively lipophillic cationic groups can be synthesized, especially from compounds comprising nitrogen or phosphorus atoms, and it is evident that many such cationic moieties could be linked in various ways to the anti-oxidant A moieties, and provide a cation that might be useful in the practice of the methods described herein. More particularly however, in many embodiments of the salts and/or cationic compounds of Formula (I) have quaternary ammonium or phosphonium moieties, having the formula:

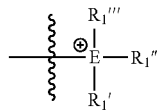

wherein:

E is a nitrogen or phosphorus atom; and $R_1'$, $R_1''$, and $R_1'''$ are each independently organic moieties comprising from 1 to 12 carbon atoms.

In many embodiments, the compounds of Formula (I) can have $R^{1'}$, $R^{1''}$, and $R^{1'''}$ are each independently selected from alkyl, aryl, heteroaryl, or aralkyl moieties, which may be unsubstituted, or optionally substituted with one or two independently selected substituent moieties, such as those described above, which include but are not limited to hydroxyl, halogen, amino, amino, dimethylamino, alkyl, hydroxyalkyl, alkoxy, alkoxylalkyl, carboxy, or carboxyalkyl moieties. Non-limiting examples of the optional substituents for $R^{1'}$, $R^{1''}$, and $R^{1'''}$ include:

i) $C_1$-$C_4$ linear branched alkyl; for example, methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$);

ii) $C_1$-$C_4$ linear or branched alkoxy; for example, methoxy ($C_1$), ethoxy ($C_2$), n-propoxy ($C_3$), iso-propoxy ($C_3$), n-butoxy ($C_4$), sec-butoxy ($C_4$), iso-butoxy ($C_4$), and tert-butoxy ($C_4$);

iii) halogen; for example, —F, —Cl, —Br, —I, and mixtures thereof;

iv) amino and substituted amino; for example, —$NH_2$, —$NH_2$, —$NHCH_3$, —$NHCH_3$, and —$N(CH_3)_2$;

v) hydroxyl; —OH;

vi) $C_1$-$C_4$ linear or branched hydroxyalkyl; for example, —$CH_2OH$, —$CH_2CH_2OH$, —$CH_2CH_2CH_2OH$, and —$CH_2CHOHCH_3$;

vii) $C_1$-$C_4$ linear or branched alkoxyalkyl; for example, —$CH_2OCH_3$, —$CH_2CH_2OCH_3$, —$CH_2CH_2CH_2OCH_3$, and —$CH_2CH(OCH_3)CH_3$;

viii) carboxy or carboxylate, for example, —$CO_2H$ or the anionic equivalent carboxylate moieties —$CO_2^-$; and xi) carboxyalkyl, for example, —$CH_2CO_2H$, —$CH_2CH_2CO_2H$, —$CH_2CO_2CH_3$, —$CH_2CH_2CO_2CH_3$, and —$CH_2CH_2CH_2CO_2CH_3$.

In related embodiments, $R_1'$, $R_1''$, and $R_1'''$ can be each independently selected from alkyl, aryl, or benzyl moieties optionally substituted with one or two independently selected hydroxyl, halogen, amino, diamino, dimethylamino, alkyl, hydroxyalkyl, alkoxy, alkoxylalkyl, carboxy, or carboxyalkyl moieties.

In other related embodiments, $R^{1'}$, $R^{1''}$, and $R^{1'''}$ can be independently selected from $C_4$-$C_{10}$ alkyl or phenyl moieties, which can optionally be substituted with one or two independently selected substituent moieites, which can include but are not limited to hydroxyl, halogen, amino, diamino, dimethylamino, alkyl, hydroxyalkyl, alkoxy, alkoxylalkyl, cyano, carboxy, or carboxyalkyl moieties. In additional embodiments, $R^{1'}$, $R^{1''}$, and $R^{1'''}$ can be independently selected from $C_4$-$C_{10}$ alkyl or phenyl moieties. In some additional embodiments $R^{1'}$, $R^{1''}$, and $R^{1'''}$ are independently selected from $C_4$-$C_{10}$ alkyl. In yet other related embodiments $R^{1'}$, $R^{1''}$, and $R^{1'''}$ are each n-$C_4H_9$ moieties.

In some embodiments of the compounds of Formula (I) having phosphonium cations, $R^{1'}$, $R^{1''}$, and $R^{1'''}$ are each phenyl moieties, to produce triphenyl phosphonium cations having the formula:

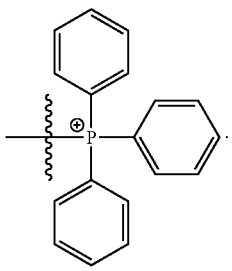 [SMILES: *[P+](c1ccccc1)(c1ccccc1)c1ccccc1 ; "."]

In alternative but related embodiments, $R^{1\prime}$, $R^{1\prime\prime}$, and $R^{1\prime\prime\prime}$ are each benzyl moieties, to produce tribenzyl phosphonium cations having the formula:

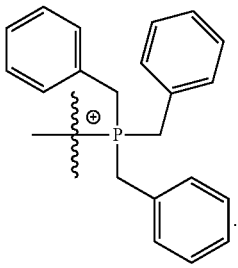

Other embodiments of the cations of Formula (I) relates to quaternary ammonium cations, i.e. wherein E is a nitrogen atom. In some such embodiments, $R^{1\prime}$, $R^{1\prime\prime}$, and $R^{1\prime\prime\prime}$ are each independently selected from alkyl, aryl, heteroaryl, or aralkyl moieties, which can be optionally substituted with one or two independently selected substituent moieties, which include but are not limited to hydroxyl, halogen, amino, dimethylamino, alkyl, hydroxyalkyl, alkoxy, alkoxylalkyl, cyano, carboxy, or carboxyalkyl moieties. Non-limiting examples of the $R^{1\prime}$, $R^{1\prime\prime}$, and $R^{1\prime\prime\prime}$ substituents include:

i) $C_1$-$C_4$ linear branched alkyl; for example, methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$);

ii) $C_1$-$C_4$ linear or branched alkoxy; for example, methoxy ($C_1$), ethoxy ($C_2$), n-propoxy ($C_3$), iso-propoxy ($C_3$), n-butoxy ($C_4$), sec-butoxy ($C_4$), iso-butoxy ($C_4$), and tert-butoxy ($C_4$);

iii) halogen; for example, —F, —Cl, —Br, —I, and mixtures thereof;

iv) amino and substituted amino; for example, —NH$_2$, —NH$_2$, —NHCH$_3$, —NHCH$_3$, and —N(CH$_3$)$_2$;

v) hydroxyl; —OH;

vi) $C_1$-$C_4$ linear or branched hydroxyalkyl; for example, —CH$_2$OH, —CH$_2$CH$_2$OH, —CH$_2$CH$_2$CH$_2$OH, and —CH$_2$CHOHCH$_3$;

vii) $C_1$-$C_4$ linear or branched alkoxyalkyl; for example, —CH$_2$OCH$_3$, —CH$_2$CH$_2$OCH$_3$, —CH$_2$CH$_2$CH$_2$OCH$_3$, and —CH$_2$CH(OCH$_3$)CH$_3$;

viii) carboxy; or carboxylate, for example, —CO$_2$H or the anionic equivalent carboxylate moieties —CO$_2^-$; and xi) carboxyalkyl, for example, —CH$_2$CO$_2$H, —CH$_2$CH$_2$CO$_2$H, —CH$_2$CO$_2$CH$_3$, —CH$_2$CH$_2$CO$_2$CH$_3$, and —CH$_2$CH$_2$CH$_2$CO$_2$CH$_3$.

In additional embodiments of the cations of Formula (I), wherein E is nitrogen, $R_1'$, $R_1''$, and $R_1'''$ are each independently selected from alkyl aryl, or benzyl moieties, which can be optionally substituted with one or two independently chosen substitutent moieties, such as those described above, which include but are not limited hydroxyl, halogen, amino, dimethylamino, alkyl, hydroxyalkyl, alkoxy, alkoxylalkyl, carboxy, or carboxyalkyl moieties.

In another embodiment $R^{1\prime}$, $R^{1\prime\prime}$, and $R^{1\prime\prime\prime}$ are independently selected from $C_4$-$C_{10}$ alkyl or phenyl moieties optionally substituted with one or two independently selected hydroxyl, halogen, amino, dimethylamino, alkyl, hydroxyalkyl, alkoxy, alkoxylalkyl, carboxy, or carboxyalkyl moieties. In one further aspect of this embodiment $R^{1\prime}$, $R^{1\prime\prime}$, and $R^{1\prime\prime\prime}$ are independently selected from $C_4$-$C_{10}$ alkyl or phenyl moieties; and in one further embodiment $R^{1\prime}$, $R^{1\prime\prime}$, and $R^{1\prime\prime\prime}$ are independently selected from $C_4$-$C_{10}$ alkyl.

In yet another embodiment of cations wherein E is nitrogen, $R^{1\prime}$, $R^{1\prime\prime}$, and $R^{1\prime\prime\prime}$ are each n-$C_4H_9$ moieties.

The "L" Linker Moiety

The cations of Formula (I) comprise a linker moiety "L", which connects the "A" moiety and the cationic moiety. The exact structure and size of the L moieties can vary considerably, and many variations of the L moieties are within the scope of the inventions disclosed herein. In some the L moieties are often organic moieties, and can comprise a wide variety of structures. In many embodiments it is desirable that the L moiety be of sufficient size and character that it provides some space and/or flexibility in the connection between the A and cation groups, but does not become of such high molecular weight so as to impair the water solubility or trans-membrane absorbability of the resulting cations.

Accordingly, in some embodiments, the L moiety, when considered as a whole, comprises from about 4 and 30 carbon atoms, or from about 4 and 20 carbon atoms. In some embodiments, the L moiety comprises from 6 to 18 carbon atoms, or from 8 to 12 carbon atoms.

In some embodiments, the L moieties can comprise only methylene or polymethylene moieties, i.e. —(CH$_2$)$_n$— moieties. Some embodiments provide L having from 5 to 24 carbon chain atoms, for example, —(CH$_2$)$_n$—, wherein the index n is from 5 to 24. Another embodiment relates to L having from 5 to 20 carbon chain atoms, for example, —(CH$_2$)$_n$—, wherein the index n is from 5 to 20. A further embodiment relates to L having from 6 to 16 carbon chain atoms, for example, —(CH$_2$)$_n$—, wherein the index n is from 6 to 16. A yet further embodiment relates to L having from 7 to 16 carbon chain atoms, for example, —(CH$_2$)$_n$—, wherein the index n is from 7 to 16. A still yet further embodiment relates to L having from 8 to 12 carbon chain atoms, for example, —(CH$_2$)$_n$—, wherein the index n is from 8 to 12. One particular example is an L unit comprising 10 methylene moieties having the formula: —CH$_2$CH$_2$CH$_2$CH$_2$CH$_2$CH$_2$CH$_2$CH$_2$CH$_2$CH$_2$—, wherein n=10.

Nevertheless, the L moieties can further comprise in the carbon chain from 1 to 10 additional atoms or groups independently selected from —O—, —S—, —S(O)—, —S(O)$_2$—, —NH—, —NCH$_3$—, —C(O)—, or —CO$_2$— moieties. For example, in some embodiments, L can be a polyalkylene glycol moiety, or a polyethylene glycol moiety, having the structure

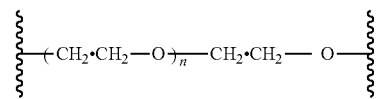

wherein n is an integer from 0 to 3.

It is to be understood that in some embodiments, the L moiety can comprise therein or thereon an additional ionic substituent moiety, so the electrical charge of the cation of Formula (I) could be increased or decreased. In particular, the L moiety can comprise an additional one or two quarternary ammonium or phosphonium moiety therein, so that the overall electrical charge of the cation of Formula I could be 2+ or 3+, so as to be a dication, or trication. Such dicationic or tricationic compounds can provide even higher water solubility and/or selectivity of absorption into mitochondria than compounds of Formula (I) that are only monocationic.

The $X^{m-}$ Anions

The salt compounds comprising the cations of Formula (I) also comprise an anion $X^m$, wherein m is an integer from 1 to 4, corresponding to monoanions, di-anions, tri-anions, and tetra-anions. The first iteration of $X^-$ relates to inorganic anion moieties. Mono-anionic inorganic anions include any halide anion, such as fluoride, chloride, bromide, or iodide; nitrate, hydrogen sulfate; dihydrogen phosphate, and the like. Dianionic inorganic cations can include carbonate, sulfate or hydrogenphosphate, and tri-anionic inorganic anions include phosphates.

In other embodiments of the $X^{m-}$ anions, the anions are organic anions. Non-limiting examples of organic anion moieties that can be employed to form the salts from the cations of Formula (I) include organosulphates such as methylsulphonate(mesylate), trifluoromethylsulfonate(triflate), benzenesulphonate, toluenesulphonate(tosylate), or purely organic anions, often formed by the neutralization of organic acids, such as fumarate, maleate, maltolate, succinate, acetate, benzoate, oxalate, citrate, or tartrate anions.

Those of ordinary skill in the art will recognize that both the cations of Formula (I) and the corresponding $X^{m-}$ anions must be combined in appropriate ratios so as to produce isolated and electrically neutral salt compounds that can be isolated and used in the methods and compositions disclosed herein. Accordingly, one way of expressing the condition of electrical neutrality when applied to the salt compounds as a whole is to recognize that such salt compounds can have the formula:

N[cation]$^{p+}$M[anion]$^{m-}$ wherein the indices M, N, m and p are each independently from 1 to 4, provided that the product (M×m)=(p×N) thereby forming a neutral salt.

Making the Compounds of the Inventions

Various synthetic methods and/or strategies can be employed in the synthesis or production of salts having cations of Formula (I) and $X^{m-}$ anions, as described above and in the examples below. Several such synthetic methods and/or strategies will be disclosed herein below.

Compounds Wherein $L_g$ is Oxygen

The [4-(tri-organophosphonium)acyloxy-2,2,6,6-tetraalkylpiperidinyloxy, free radical] salts of the present invention have the formula:

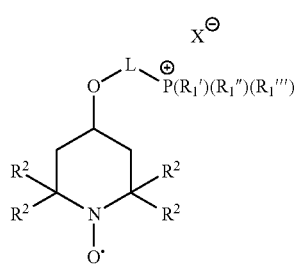

wherein $R_1'$, $R_1''$, $R_1'''$, $R^2$, L, and X are defined elsewhere. These compounds can be synthesized by the following generic procedure outlined in Scheme I.

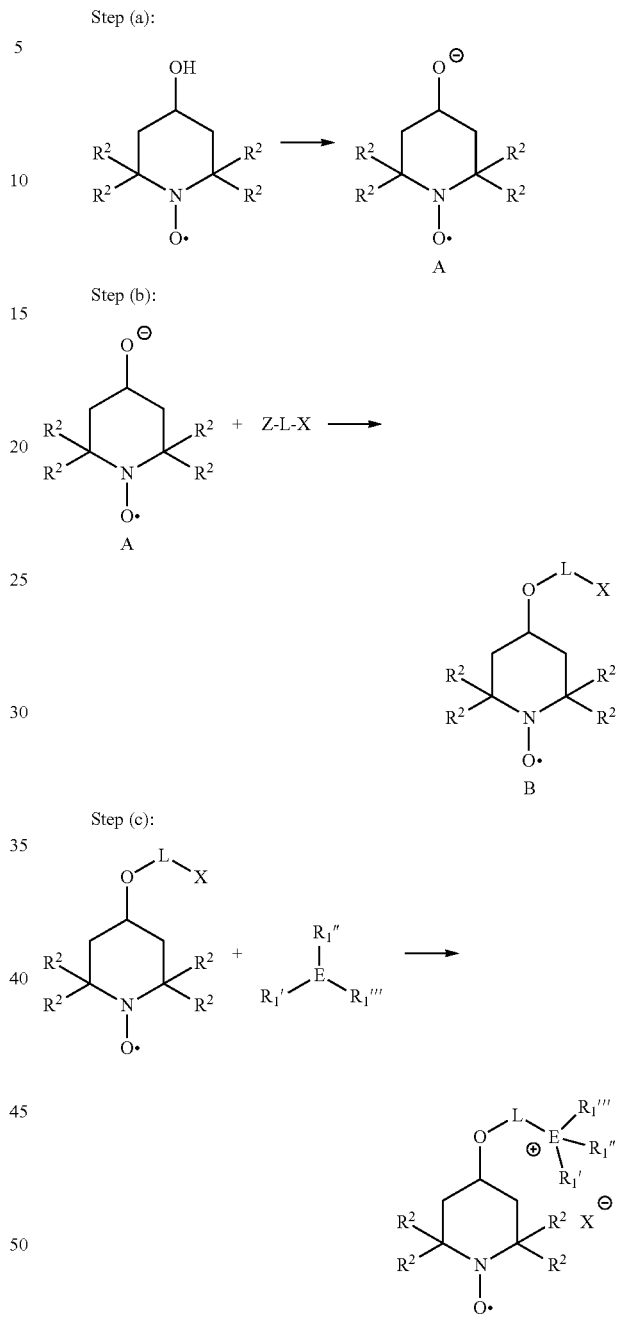

The 4-substituted -2,2,6,6-tetraalkylpiperidinyloxy moieties used as starting materials for step (a) of Scheme I are well known in the art as "Tempol" derivatives and many such compounds are known in the art and/or readily commercially available, especially compounds wherein all $R^2$ groups are methyls.

Step (a) encompasses removal of an $H^+$ cation from the starting material with a strong base, with generation of the corresponding 4-alkoxy anion. The proton can be removed by any strong organic or inorganic base which is convenient and which does not affect the $R^2$ substituents. Non-limiting examples of organic bases include alkyl or aryl lithium reagents, such as phenyl lithium, methyl lithium, n-butyl lithium, tert-butyl lithium, sodium amide, lithium amide, lithium diisopropylamide, lithium dimethylamide, lithium diethylamide, and the like. The formation of the 4-alkoxy anion can be conducted in the cold, i.e. at room temperature or from 0° C. to −78° C.

Non-limiting examples of inorganic bases include NaOH, KOH, LiOH, Ca(OH)$_2$, Na$_2$CO$_3$, K$_2$CO$_3$, and the like. One embodiment which is described herein below utilizes NaH as the base. Other hydride bases, inter alia, KH can be utilized especially when low temperature conditions and solvent compatibility cause more reactive bases to be used. In addition, strong inorganic bases can be used to form organic bases from polar aprotic solvents, inter alia, dimethyl sulfoxide, N,N-dimethylacetamide, and hexamethylphosphoric triamide, for example, a dimsyl anion from dimethyl sulfoxide.

Any non-reactive or aprotic solvent or mixtures of solvents can be used for Step (a). Non-limiting examples of solvents include alkane solvents, inter alia, pentane, iso-pentane, hexane, heptane, octane, isooctane, and the like; aromatic hydrocarbon solvents, inter alia, benzene, toluene, and xylene (all isomers); ethers, inter alia, diethyl ether, tetrahydro-furan, and dioxane; and various fluorinated hydrocarbons. In addition, polar aprotic solvents can be used, inter alia, dimethyl sulfoxide, dimethylformamide, N,N-dimethylacetamide, and hexamethylphosphoric triamide.

In addition, combinations of solvents can be used. For example, typically once the anion is generated, the formulator can proceed to Step (b) without necessarily having to isolate the alkoxide, therefore, a second co-solvent may be used which enhances the solubility of the reagents used in Step (b) without affecting the formation of the anion.

Step (b) encompasses attaching a linker group L to the alkoxide generated in Step (a). The 4-alkoxide is reacted with a linker molecule L having two reactive leaving groups; Z and X. The leaving groups may be the same or different.

L is a linking group comprising from 4 to 30 carbon atoms as described herein. Z and X can be any suitable leaving group which is sufficiently reactive to allow attachment of the tether without loss of the free radical moiety. Non-limiting examples of suitable leaving groups include halogens: iodine, bromine, and chlorine; sulphonyl leaving groups, inter alia, methylsulphonyl(mesyl), ethylsulphonyl, benzenesulphonyl, toluenesulphonyl(tosyl), and the like.

Non-limiting examples of compounds having two leaving groups that can be used to as reagents in forming the linking group between the free radical portion of the molecule and the quaternary ammonium or phosphonium moiety include:

i) α,ω-di-bromoalkanes, inter alia, 1,4-dibromobutane, 1,5-dibromopentane, 1,6-dibromohexane, 1,7-dibromoheptane, 1,8-dibromooctane, 1,9-di-bromononane, and 1,10-dibromodecane;

ii) α,ω-di-chloroalkanes, inter alia, 1,4-dichlorobutane, 1,5-dichloropentane, 1,6-dichlorohexane, 1,7-dichloroheptane, 1,8-dichlorooctane, 1,9-di-chlorononane, and 1,10-dichlorodecane;

iii) α,ω-di-iodoalkanes, inter alia, 1,4-diiodobutane, 1,5-diiodopentane, 1,6-diiodohexane, 1,7-diiodoheptane, 1,8-diiodooctane, 1,9-di-iodononane, and 1,10-diiododecane;

iv) α,ω-mixed leaving group alkanes, inter alia, 1-bromo-4-chlorobutane, 1-bromo-5-chloropentane, 1-bromo-6-chlorohexane, 1-bromo-10-chloro-decane, 1-iodo-4-chlorobutane, 1-iodo-5-chloropentane, 1-iodo-6-chloro-hexane, 1-iodo-10-chlorodecane, 1-iodo-4-bromobutane, 1-iodo-5-bromo-pentane, 1-iodo-6-bromohexane, 1-iodo-10-bromodecane, 1-toluenesulphonyl-4-chlorobutane, 1-toluenesulphonyl-5-chloropentane, 1-toluene-sulphonyl-6-chlorohexane, 1-toluenesulphonyl-10-chlorodecane, 1-bromo-4-toluenesulphonylbutane, 1-bromo-5-toluenesulphonylpentane, 1-bromo-6-toluenesulphonylhexane, 1-bromo-10-toluenesulphonyldecane, 1-azido-4-chlorobutane, 1-azido-5-chloropentane, 1-azido-6-chlorohexane, and 1-azido-10-chlorodecane.

The formulator can take advantage of the differential reactivity of leaving groups when using α,ω-mixed leaving group alkanes for the formation of the tether. However, the formulator may wish to insert an optional Step (b)(ii) into the process for preparing the compounds of the present invention. For example, the formulator can, once intermediate B is formed, increase the reactivity of leaving group X in order to adjust for any lesser reactivity that the reagent which introduces the quaternary ammonium or phosphonium salt has. For example, in the following step 1-iodo-4-chlorobutane is used to attach the first end of the tether to the free radical containing unit taking advantage of the increased reactivity of iodine as a preferred leaving group over chlorine.

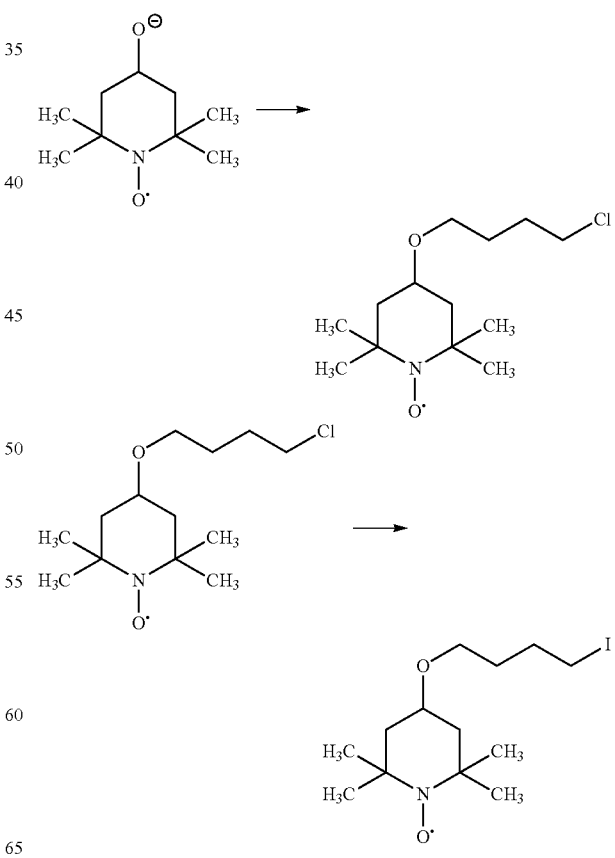

wherein chlorine is replaced by iodine.

Non-limiting examples of solvents which can be used for Step (b), as well as any optional steps, inter alia, Step (b)(i), include alkane solvents, inter alia, pentane, iso-pentane, hexane, heptane, octane, isooctane, and the like; aromatic hydrocarbon solvents, inter alia, benzene, toluene, and xylene (all isomers); ethers, inter alia, diethyl ether, tetrahydro-furan, and dioxane; and various fluorinated hydrocarbons. In addition, polar aprotic solvents can be used, inter alia, dimethyl sulfoxide, dimethylformamide, N,N-dimethylacetamide, and hexamethylphosphoric triamide.

Step (c) encompasses forming a quaternary ammonium or phosphonium salt at the end of the linking unit opposite the end which contains the nitroxide or amine oxide moiety. For example, formation of a phosphonium salt:

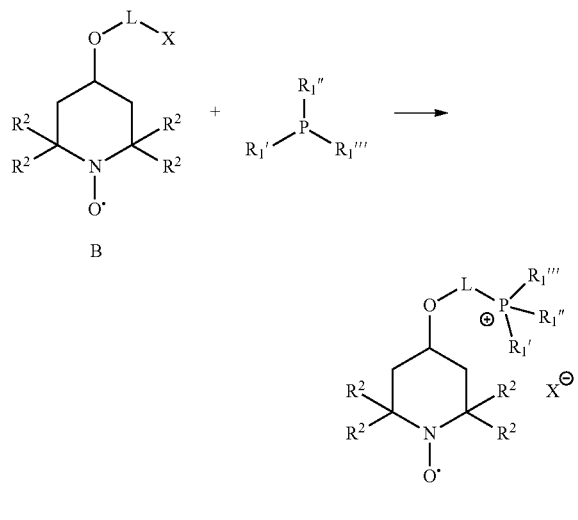

B or formation of an quaternary ammonium salt:

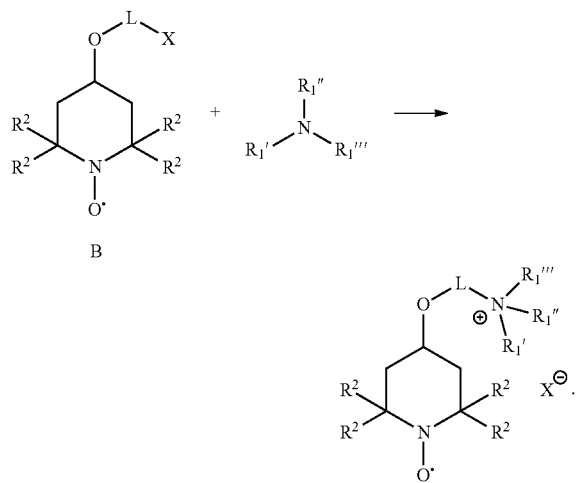

B

However, in the case of quaternary ammonium salt containing products, Step (c) may optionally be divided into two separate steps, Step (c)(i) and Step (c)(ii), which can be conducted either without isolation of the intermediate C or which can be conducted as two discrete steps, wherein intermediate C is isolated prior to quaternization, for example:

Step (c)(i):
Formation of a tertiary amine by displacement of the leaving group X to form intermediate C:

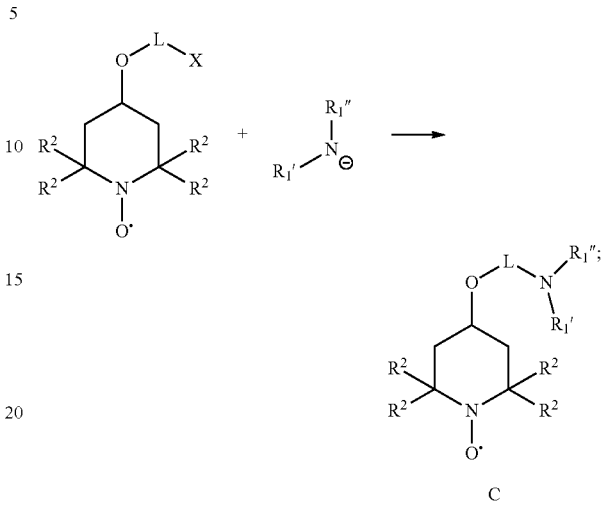

C which can be isolated if desired, followed by quaternization of the amine to form the final quaternary ammonium salt:
Step (c)(ii):

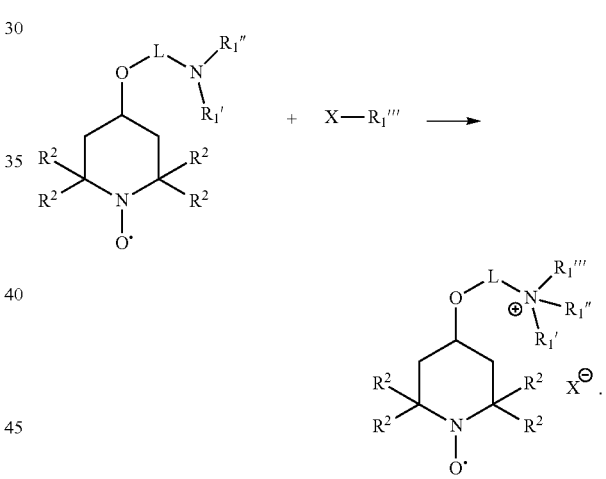

The formulator can chose the leaving group X which comprises the alkylating agent in Step (c)(ii) to be the same as the leaving group that is displaced in Step (c)(i) or to take the opportunity to provide a different leaving group which results in the potential source of a different counter ion for the quaternary ammonium ion. However, the formulator can alternatively choose to provide the final anion by exchanging the anion present as a result of the reaction which occurs in Step (c) with another anion, and this can be done by exposing the final product to a counter ion exchange system, for example, an ion exchange resin.

In the case of forming a phosphonium salt, a tri-substituted phosphine can be directly reacted with compounds such as intermediate B to form final compounds. Examples of this reaction are found in Examples 1 and 2 herein below.

Depending upon the reactivity of the leaving group X and how nucleophilic the phosphine adduct is toward leaving group X, the reaction can be conducted over a wide range of temperatures. A first embodiment of this phosphonium forming step encompasses the reaction taking place in a refluxing solvent. Because a salt if formed, it is advantageous for the formulator to select a solvent wherein the starting materials have good solubility, but the product which forms is either insoluble or has a reduced solubility. In this way when a stoichiometric excess of one starting reagent is used, the excess will potentially remain in solution while the desired product precipitates as an insoluble material. In addition, a co-solvent in which the product is known to be insoluble but which affords solubility to any unreacted starting material may be added to cause precipitation of the product. These same principles apply to the formation and isolation of quaternary ammonium salts formed whether in Step (c), or by way of alternative Step (c)(i) and Step (c)(ii).

Step (c) can be conducted in any non-nucleophilic solvent which allows for the adequate formation of the desired product.

Suitable solvents or mixtures of solvents can be used for Step (c). Non-limiting examples of solvents include alkane solvents, inter alia, pentane, iso-pentane, hexane, heptane, octane, isooctane, and the like; aromatic hydrocarbon solvents, inter alia, benzene, toluene, and xylene (all isomers); ethers, inter alia, diethyl ether, tetrahydro-furan, and dioxane; ketones, inter alia, acetone, methyl ethyl ketone, 3-pentanone; halogenated solvents, inter alia, dichloromethane, chloroform, carbon tetrachloride, 1,1-dichloroethane, 1,2-dichloroethane, 1,1,1-trichloroethane, and various fluorinated hydrocarbons. In addition, polar aprotic solvents can be used, inter alia, dimethyl sulfoxide, dimethylformamide, N,N-dimethylacetamide, and hexamethylphosphoric triamide.

In some instances reactivity may be increased by the addition of a protic solvent, inter alia, water, methanol, ethanol, and the like, which can aid in solvation and separation of ion pairs, however, these adjustments to Step (c) are within the scope of the artisan and can be made without undue experimentation.

Scheme II outlines the preparation of a compound disclosed herein which is further described in detail in Example 1.

Scheme II

Reagents and conditions: (a) NaH, benzene; reflux, 24 hr.

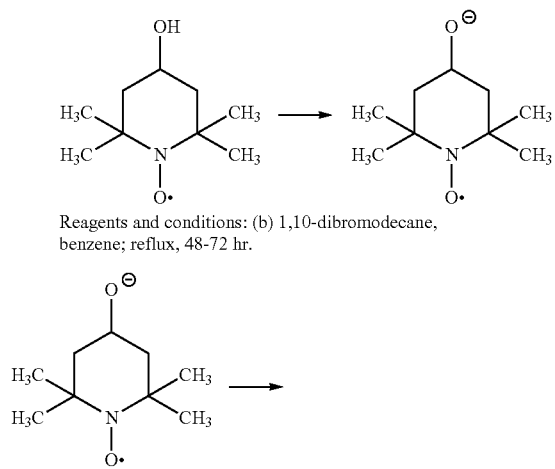

Reagents and conditions: (b) 1,10-dibromodecane, benzene; reflux, 48-72 hr.

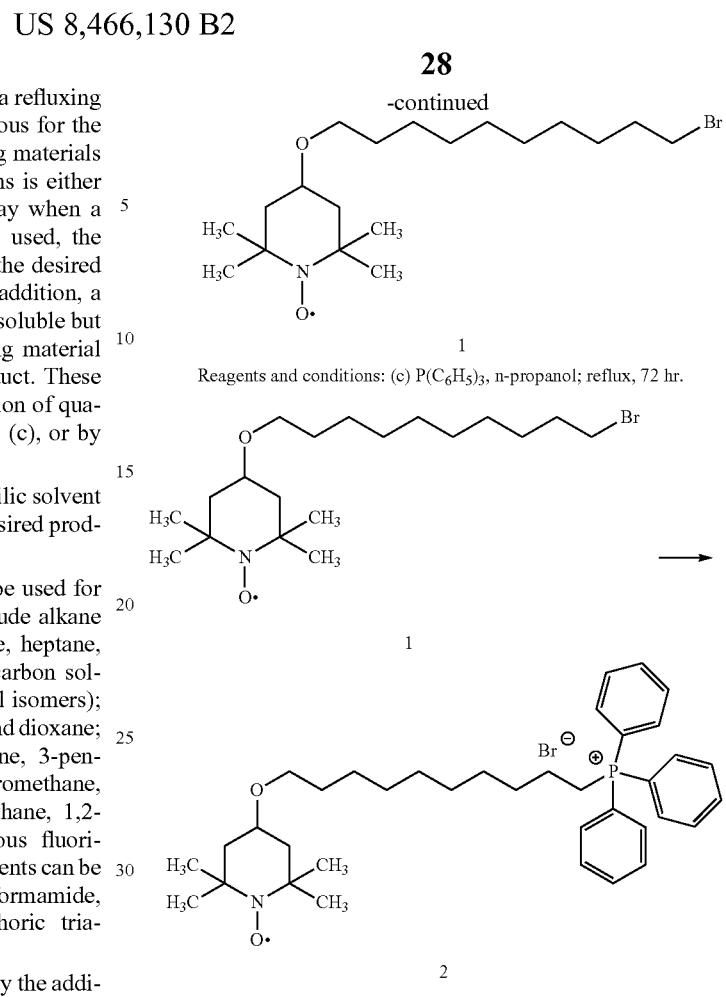

Reagents and conditions: (c) P(C$_6$H$_5$)$_3$, n-propanol; reflux, 72 hr.

Example 1

[4-(10-triphenylphosphonium)decyloxy-2,2,6,6-tetramethylpiperidinyloxy, free radical]bromide (2) (also known as MitoT-10, or CPC-410)

Tempol (0.01 mol) was added to a three-neck flask containing 100 ml dry benzene that is maintained at nitrogen atmosphere. To the flask, sodium hydride (0.015 mol) was added and kept refluxed for 24 hrs. The flask was cooled in ice bath and added 1,10-dibromodecane (0.02 mol) in one portion. The refluxing was then resumed for another 72 hrs. The contents of the flask was cooled in ice bath and added 25 ml water and transferred to a separatory funnel. The red upper benzene layer was separated, dried over anhydrous magnesium sulfate and solvent removed by rotory evaporation to get a red oil. The oil was purified by column chromatography on silica gel 60. The material was added to the column and eluted first with about 150 ml hexane that removed the excess of dibromodecane. The desired bromodecanoyl ether of Tempol was eluted with a mixture of hexane and ether (90:10). The red eluate was collected and was found to be pure on thin layer chromatography plates developed using the same solvent mixture. The yield was 0.008 mol (80%).

The bromoether of Tempol 0.008 mol and triphenyl phosphine (0.01 mol) were taken in a flask and added 20 ml of n-propanol. The contents of the flask was kept refluxed under nitrogen for 72 hrs. The flask was cooled and the solvent was removed by rotory evaporation. The residue was dissolved in 10 ml dichloromethane and added to 100 ml ether with stiffing. The precipitated product was collected by decantation of the solvent. The residual semisolid was then purified on silica gel 60 column eluting first with dichloromethane and the desired product was eluted with a mixture of dichloromethane and methanol (90:10). Homogeneous fractions combined and solvent removed to get a red-brown semisolid with a yield of 65%. Purity was ascertained by LC-MS (mass=573.4).

Scheme III outlines the preparation of a compound disclosed herein which is further described in detail in Example 2.

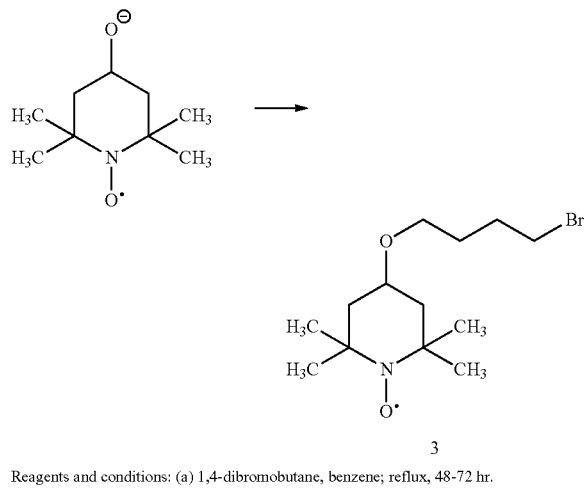

Reagents and conditions: (a) 1,4-dibromobutane, benzene; reflux, 48-72 hr.

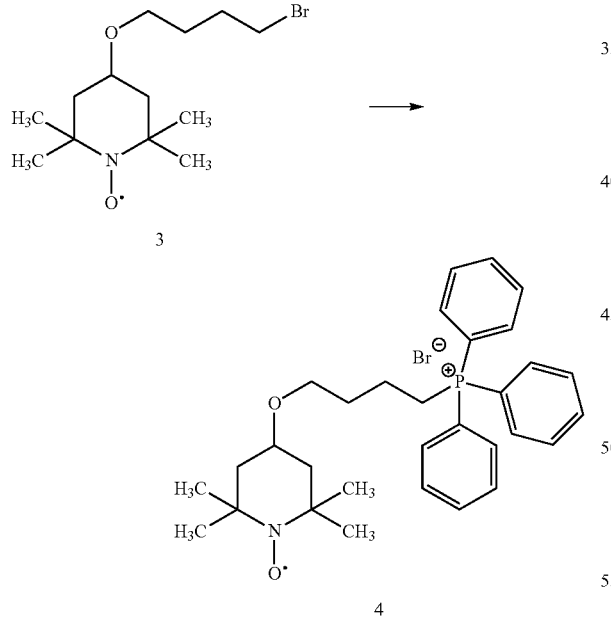

Reagents and conditions: (b) P(C$_6$H$_5$)$_3$, dioxane; reflux, 72 hr.

Example 2

[4-(4-triphenylphosphonium)butoxy-2,2,6,6-tetramethylpiperidinyloxy, free radical]bromide (4)

Preparation of 4-(4-bromobutoxy)-2,2,6,6-tetramethylpiperidinyloxy, free radical (3): To a 250-mL 3-neck flask equipped with a reflux condenser and nitrogen inlet line was charged 4-hydroxy-2,2,6,6-tetramethylpiperidinyloxy, free radical [tempol] (3.44 g, 20 mmol) and dry benzene (100 mL). Sodium hydride (0.72 g, 30 mmol) was slowly added. Once the addition was complete, the reaction was brought to reflux for 24 hours. The resulting suspension was cooled in an ice bath and 1,4-dibromobutane (8.6 g, 40 mmol) was added and the solution was again brought to reflux for 24 hours. After the reaction was complete the reaction solution was cooled and water (50 mL) was added. The contents of the reaction vessel were transferred to a separatory funnel and extracted with diethyl ether (100 mL). The organic layer was decanted and dried over MgSO$_4$ then concentrated under reduced pressure to afford the crude product containing unreacted di-bromide. The product was purified over silica [gradient eluetion:100% hexane to 1:1 hexane/diethyl ether]. The solvent was removed in vacuo to afford 5.0 g (82% yield) of the desired product as a red oil. TLC (hexane/diethyl ether 1:1) one spot at R$_f$ 0.75).

Preparation of [4-(4-triphenylphosphonium)dibutoxy-2,2,6,6-tetramethyl-piperidinyloxy, free radical]bromide (4): To a 3-neck flask equipped with a reflux condenser and nitrogen inlet tube was charged 4-(10-bromobutoxy)-2,2,6,6-tetramethylpiperidinyloxy, free radical, 3, (5 g, 16.4 mmol) and dioxane (50 mL). The solution was stirred and triphenylphosphine (8 g, 30.5 mmol) was added. The mixture was then brought to reflux for 24 hours. The reaction solution was cooled and the solvent removed under reduced pressure. The residue was treated with diethyl ether (200 mL), the organic layer was decanted and the residue dissolved in CH$_2$Cl$_2$ (10 mL) then added to a flask containing diethyl ether (100 mL). The precipitate was collected, dissolved in CH$_2$Cl$_2$ and re-precipitated with diethyl ether. This procedure was repeated 3 additional times to afford 6.5 g (60% yield) of the desired product as a fluffy brown solid that is hydroscopic. The presence of the free radical was confirmed by EPR spectroscopy. LCMS MH$^+$ 489.5.

Scheme IV outlines an example of the preparation of compounds disclosed herein wherein the linking unit is tethered to the free radical portion of the final compound by way of an ester linkage.

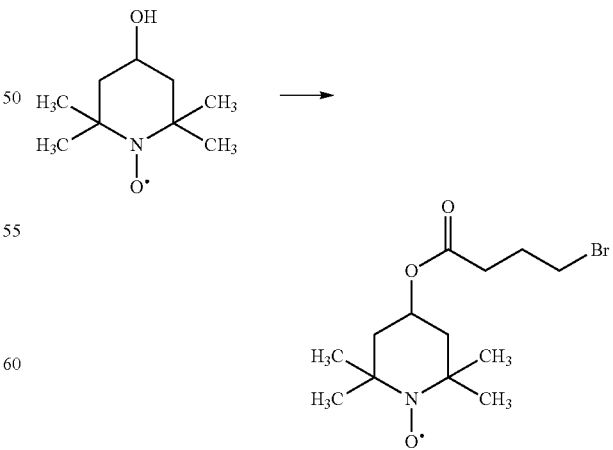

Reagents and conditions: (a) 4-bromobutyryl chloride, benzene; reflux.

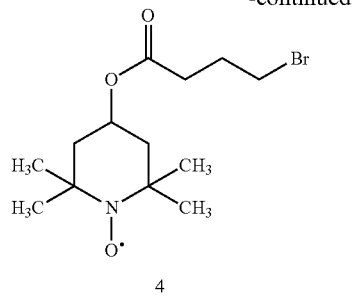

4

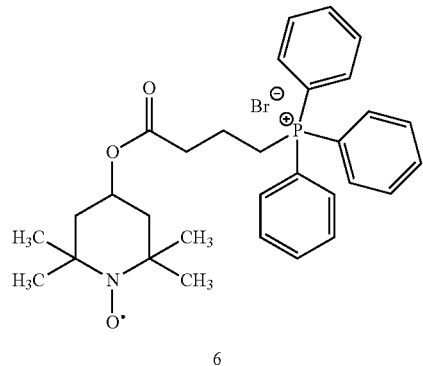

6

Reagents and conditions: (b) P(C₆H₅)₃, dioxane; reflux.

Example 3

4-[4-(Triphenylphosphonium)butyryloxy-2,2,6,6-tetramethylpiperidinyloxy, free radical]bromide (6)

Preparation of 4-(4-bromobutyryloxy)-2,2,6,6-tetramethylpiperidinyloxy, free radical (5): To a 250 mL 3-neck flask equipped with a reflux condenser and nitrogen inlet line was charged 4-hydroxy-2,2,6,6-tetramethylpiperidinyloxy, free radical [tempol] (3.44 g, 20 mmol), triethylamine (2.22 g, 22 mmol) and dry benzene (100 mL). The solution was cooled in an ice bath to 0° C. 4-Bromobutyryl chloride (3.9 g, 21 mmol) was added slowly. After the addition is complete, the solution was allowed to warm to room temperature and stir over night. The contents of the reaction vessel were transferred to a separatory funnel and extracted with water (50 mL), brine (50 mL), then dried over $Na_2SO_4$. The solvent was removed in vacuo to afford the desired product which can be used for the next step without further purification.

Preparation of 4-[4-(triphenylphosphonium)butyryloxy-2,2,6,6-tetramethyl-piperidinyloxy, free radical]bromide (6): To a 3-neck flask equipped with a reflux condenser and nitrogen inlet tube was charged 4-(4-bromobutyryloxy)-2,2,6,6-tetramethylpiperidinyloxy, free radical, 5, (6.42 g, 20 mmol) and dioxane (50 mL). The solution was stirred and triphenylphosphine (10.5 g, 40 mmol) was added. The mixture was then brought to reflux for 24 hours. The reaction solution was cooled and the solvent removed under reduced pressure. The residue was treated with diethyl ether (200 mL), the organic layer was decanted and the residue dissolved in $CH_2Cl_2$ (10 mL) then added to a flask containing diethyl ether (100 mL). The precipitate was collected, dissolved in $CH_2Cl_2$ and re-precipitated with diethyl ether. This procedure was repeated 3 additional times to afford the desired product.

Scheme V outlines an example of the preparation of exemplary compounds disclosed herein which is further described in detail in Example 4.

Scheme V

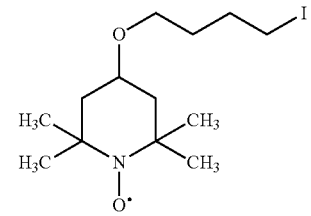

3

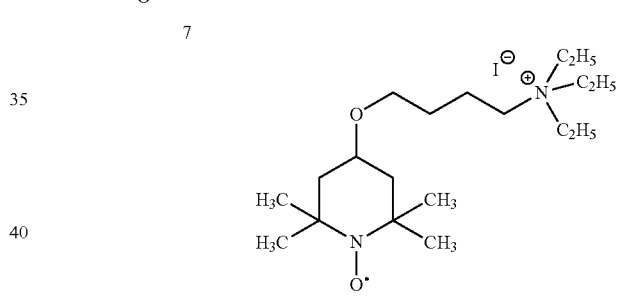

Reagents and conditions: (a) NaI, acetone; reflux, 24 hr.

Reagents and conditions: (b) triethylamine, dioxane; reflux.

Example 4

{4-[4-(N,N,N-Triethylammonium)butoxy]-2,2,6,6-tetramethylpiperidinyloxy, free radical}iodide Preparation of 4-(4-iodobutoxy)-2,2,6,6-tetramethylpiperidinyloxy, free radical (7): To a 250 mL 3-neck flask equipped with a reflux condenser and a nitrogen inlet line is charged 4-(4-bromobutoxy)-2,2,6,6-tetramethylpiperidinyloxy, free radical, 3, (6.12 g, 20 mmol) and anhydrous acetone (50 mL). Sodium iodide (15 g, 100 mmol) that has been dried in an oven and stored in a desiccator is added in one portion. The reaction is brought to reflux for 1 hour then allowed to cool and stir overnight. Water (5 mL) is added and the volume of solvent is reduced in vacuo to approximately 20 mL. The resulting solution is extracted with $CH_2Cl_2$ (3×25 mL), the organic layers combined, dried over $MgSO_4$ and concentrated in vacuo to afford the desired product which is used without further purification.

Preparation of {4-[4-(N,N,N-triethylammonium)butoxy]-2,2,6,6-tetramethylpiperidinyloxy, free radical}iodide (8): To a 250 mL 3-neck flask equipped with a reflux condenser is charged 4-(4-iodobutoxy)-2,2,6,6-tetramethyl-piperidinyloxy, free radical, 7, (7.08 g, 20 mmol), triethylamine (20.2 g, 27.8 mL, 200 mmol), and benzene (100 mL). The reaction is warmed to 60° C. and allowed to stir overnight. The reaction is cooled to room temperature after which the reaction is poured into diethyl ether (200 mL). The resulting solution is stirred and the organic layer decanted. The solid that remains is triturated with diethyl ether, the solid collected and dried to afford the desired compound.

Compounds Wherein $L_g$ is —NH—

The [4-(triphenylphosphonium)acylamino-2,2,6,6-tetraalkylpiperidinyloxy, free radical]salts of the present invention have the formula:

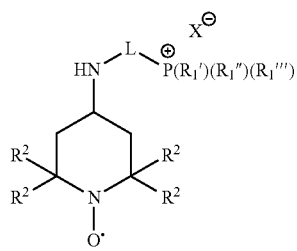

wherein $R_1'$, $R_1''$, $R_1'''$, $R^2$, L, and X are further defined herein above. These compounds can be made by the following generic procedure outlined in Scheme VI.

Scheme VI

Step (d):

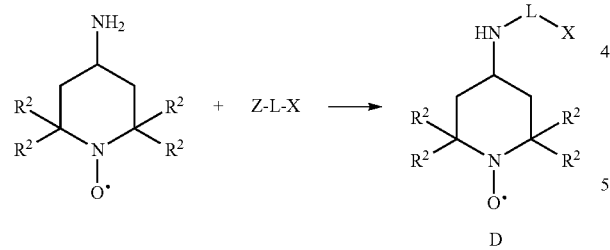

Step (e):

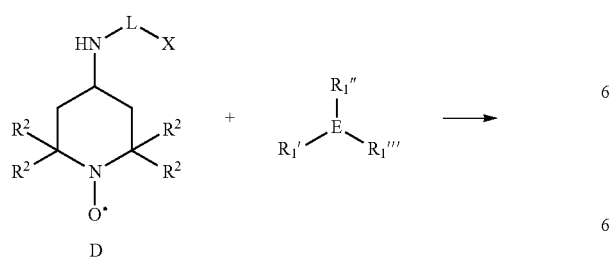

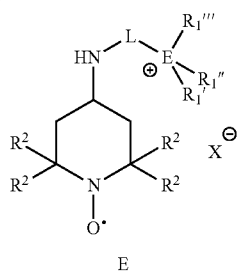

Step (d) encompasses attaching a tether to the free radical containing portion of the molecule. The 4-amino-2,2,6,6-tetraalkylpiperidinyloxy free radical is reacted with a molecule having two reactive leaving groups; Z and X. The leaving groups may be the same or different, however, Z is the group which reacts first to form the 4-acyloxy-2,2,6,6-tetraalkylpiperidinyloxy free radical intermediate, D, as depicted in Step (d) of Scheme VI.

Because in Step (e) described herein, a quaternary ammonium salt or phosphonium salt is formed, it is convenient for the formulator to utilize as a leaving group X, a unit that can form a stable anion and therefore act as the counter ion for the quaternary ammonium or phosphonium salt that is formed.

L is a linking group comprising from 4 to 30 carbon atoms as described elsewhere herein Reaction procedures, conditions, solvents, reaction times, etc are similar to those employed with similar compounds wherein Lg is oxygen, and adjusting such parameters to produce useable yields of the desired products is within the level of skill of those skilled in the art of organic synthesis.

Scheme VII outlines an example of the preparation of amide compounds disclosed herein wherein the linking unit is tethered to the free radical portion of the final compound by way of an amide linkage. These compounds can be prepared by the following procedure outlined herein below.

Scheme VII

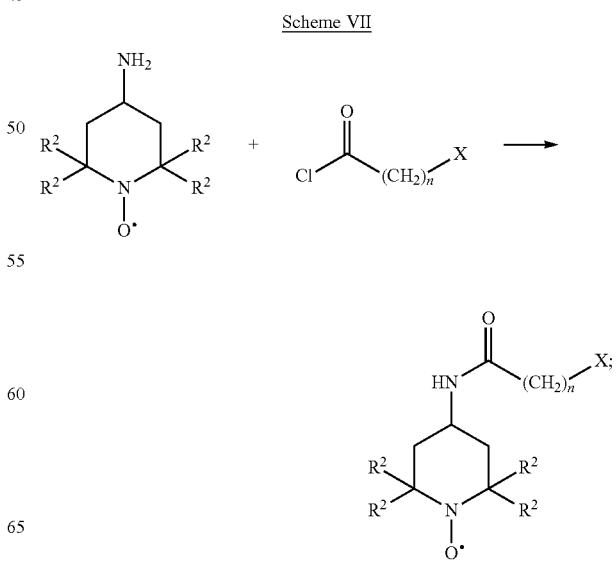

35
-continued

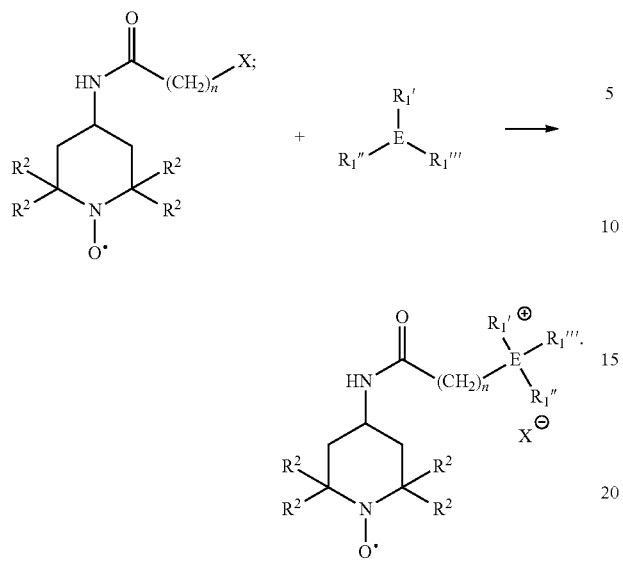

Scheme VIII

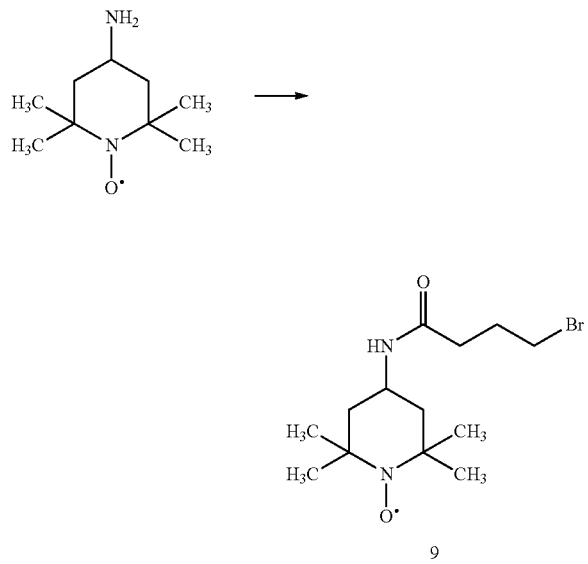

Reagents and conditions: (a) 4-bromobutyryl chloride, CH$_2$Cl$_2$; rt, 48-72 hr.

36
-continued

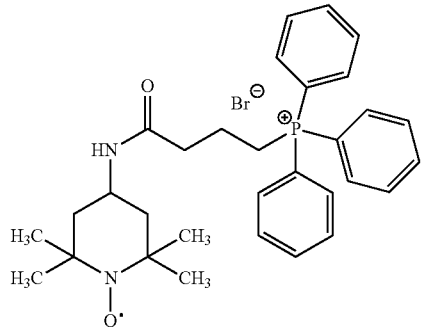

Reagents and conditions: (b) P(C$_6$H$_5$)$_3$, dioxane; reflux, 72 hr.

Example 5

{4-[4-(Triphenylphosphonium)butyrylamide-2,2,6,6-tetramethylpiperidinyloxy]free radical}bromide Preparation of 4-(4-bromobutyrylamide)-2,2,6,6-tetramethylpiperidinyloxy, free radical (9): To a 250 mL 3-neck flask equipped with a reflux condenser and nitrogen inlet line is charge 4-amino-2,2,6,6-tetramethylpiperidine-1-oxyl, free radical [4-amino-tempo] (3.44 g, 20 mmol), triethylamine (2.22 g, 22 mmol) and dry benzene (100 mL). The solution is cooled in an ice bath to 0° C. 4-Bromobutyryl chloride (3.9 g, 21 mmol) is added slowly. After the addition is complete, the solution is allowed to warm to room temperature and stir over night. The contents of the reaction vessel is transferred to a separatory funnel and extracted with water (50 mL), brine (50 mL), then dried over Na$_2$SO$_4$. The solvent is removed in vacuo to afford the desired product which can be used for the next step without further purification.

Preparation of {4-[4-(triphenylphosphonium)butyrylamide-2,2,6,6-tetramethylpiperidinyloxy]free radical}bromide (10): To a 3-neck flask equipped with a reflux condenser and nitrogen inlet tube is charged 4-(4-bromobutyrylamide)-2,2,6,6-tetramethylpiperidinyloxy, free radical, 9, (6.4 g, 20 mmol) and dioxane (50 mL). The solution is stirred and triphenylphosphine (10.5 g, 40 mmol) is added. The mixture is then brought to reflux for 24 hours. The reaction solution is cooled and the solvent removed under reduced pressure. The residue is treated with diethyl ether (200 mL), the organic layer is decanted and the residue dissolved in CH$_2$Cl$_2$ (10 mL) then added to a flask containing diethyl ether (100 mL). The precipitate is collect, dissolved in CH$_2$Cl$_2$ and re-precipitated with diethyl ether. This procedure is repeated 3 additional times to afford the desired product.

The examples herein above encompass free radical moieties derived from 6-member ring starting materials. The disclosed compounds also encompass free radical moieties derived from 5-member ring starting materials, for example:

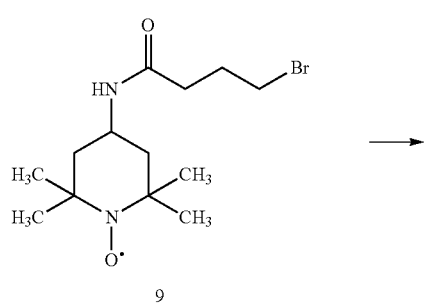

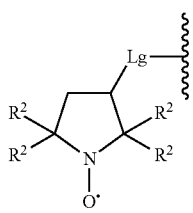

wherein $R_1'$, $R_1''$, $R_1'''$, $R^2$, L, $L_g$, E, and X are further defined herein above. Such compounds, wherein are well known in the art as "Proxyl" compounds and many suitable precursors of the Proxyl "A" moiety are readily commercially available from standard suppliers of fine chemicals, such as Aldrich-Sigma of Milwaukee Wis. For example, the following precursors of a Proxyl moiety are commercially available:

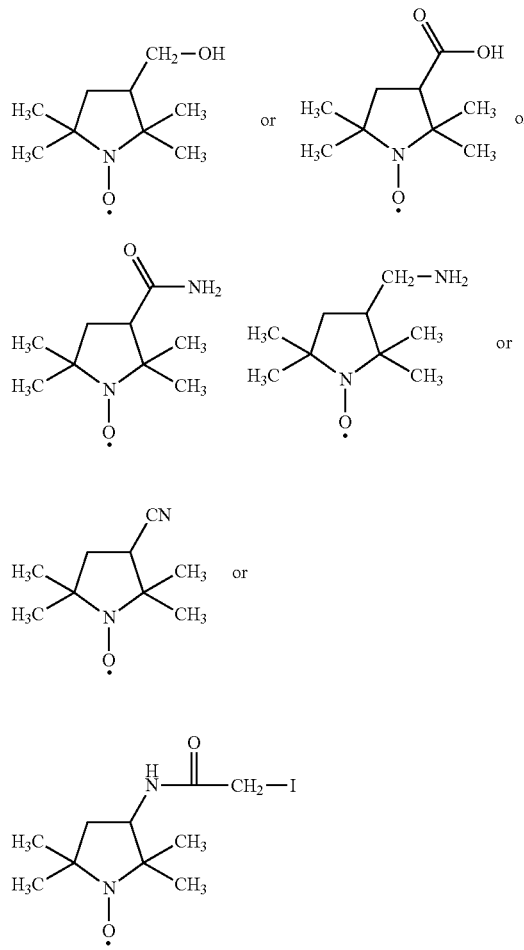

The preparation of compounds starting from such "Proxyl" starting materials can be carried out in analogy to the procedures outlined in Schemes I and II above, and other similar procedures as would be well within the capabilities of one of ordinary skill in the art of synthetic organic chemistry.

Scheme VIII outlines an example of the preparation of compounds disclosed herein wherein the free radical moiety is derived from a 5-member ring starting material.

Scheme IX

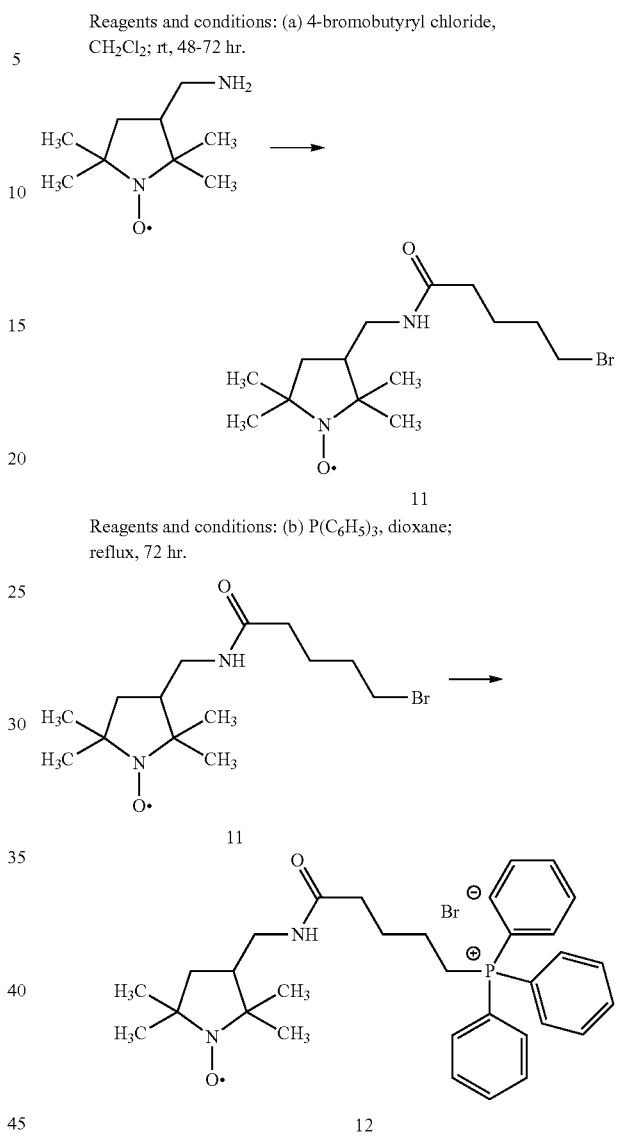

Example 6

({3-[4-(Triphenylphosphonium)butyrylamide]methyl-2,2,5,5-tetramethyl-pyrrolidinyloxy}free radical)bromide Preparation of 3-(4-bromobutyrylamide)methyl-2,2,5,5-tetramethylpyrrolidin-yloxy, free radical (11): To a 250 mL 3-neck flask equipped with a reflux condenser and nitrogen inlet line is charge 3-aminomethyl-2,2,6,6-tetramethylpiperidine-1-oxyl, free radical [3-aminomethylproxyl] (3.42 g, 20 mmol), triethylamine (2.22 g, 22 mmol) and dry benzene (100 mL). The solution is cooled in an ice bath to 0° C. 4-Bromobutyryl chloride (3.9 g, 21 mmol) is added slowly. After the addition is complete, the solution is allowed to warm to room temperature and stir over night. The contents of the reaction vessel is transferred to a separatory funnel and extracted with water (50 mL), brine (50 mL), then dried over Na$_2$SO$_4$. The solvent is removed in vacuo to afford the desired product which can be used for the next step without further purification.

Preparation of ({3-[4-(triphenylphosphonium)butyrylamide]methyl-2,2,5,5-tetramethylpyrrolidinyloxy}free radical)bromide (12): To a 3-neck flask equipped with a reflux condenser and nitrogen inlet tube is charged 3-(4-bromobutyrylamide)methyl-2,2,5,5-tetramethylpyrrolidinyloxy, free radical, 11, (6.68 g, 20 mmol) and dioxane (50 mL). The solution is stirred and triphenylphosphine (10.5 g, 40 mmol) is added. The mixture is then brought to reflux for 24 hours. The reaction solution is cooled and the solvent removed under reduced pressure. The residue is treated with diethyl ether (200 mL), the organic layer is decanted and the residue dissolved in CH$_2$Cl$_2$ (10 mL) then added to a flask containing diethyl ether (100 mL). The precipitate is collect, dissolved in CH$_2$Cl$_2$ and re-precipitated with diethyl ether. This procedure is repeated 3 additional times to afford the desired product.

Another example of a related synthesis of compounds wherein Proxyl groups can be linked to phosphonium cations by ether groups derived from glycols, to form compounds within the scope of the invention is shown below in Scheme IX:

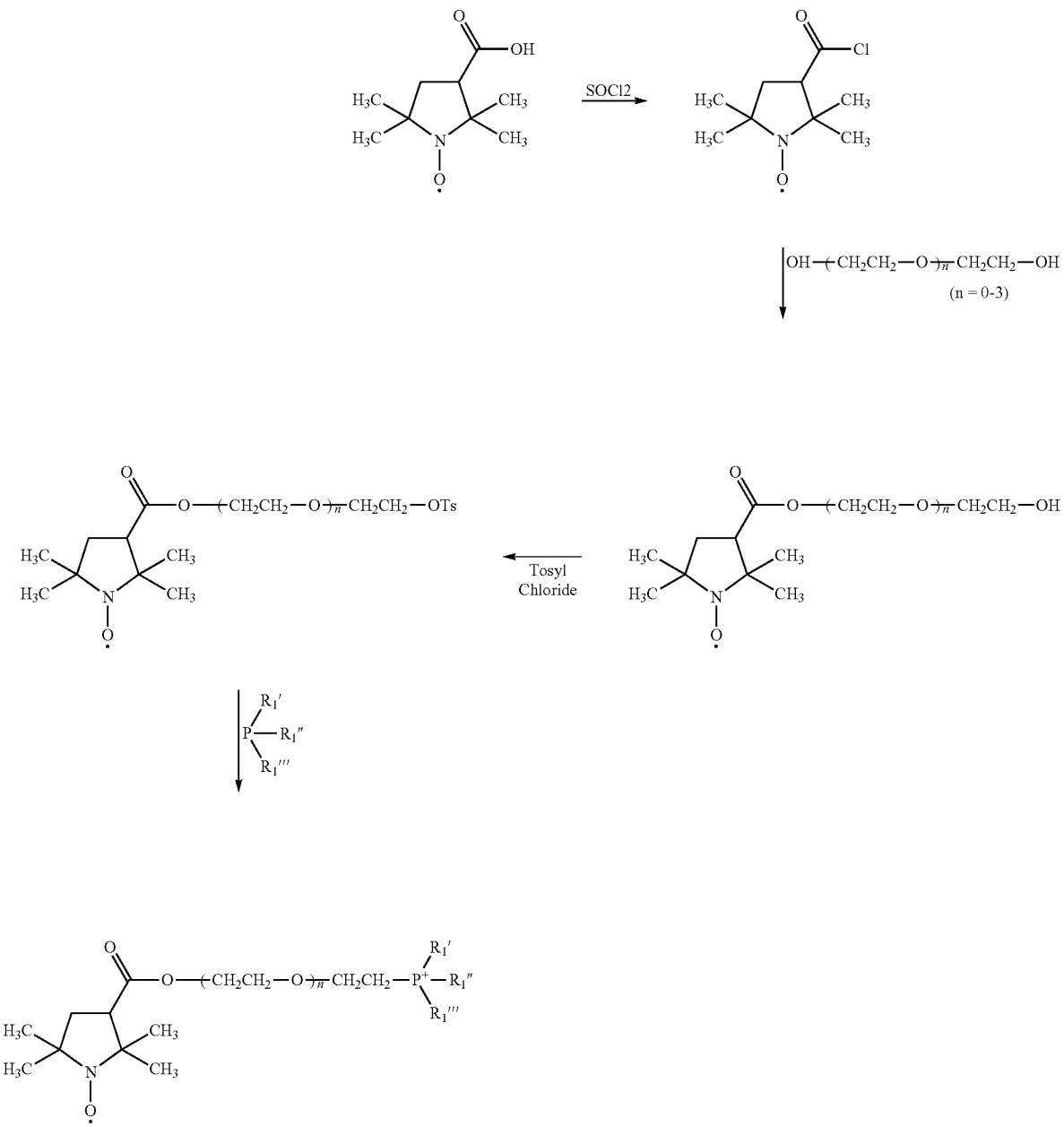

Scheme IX

Another example of a related synthesis of compounds wherein Proxyl groups can be linked to phosphonium cations by moieties derived from glycols, to form compounds within the scope of the invention is shown below in Scheme X:

Scheme X

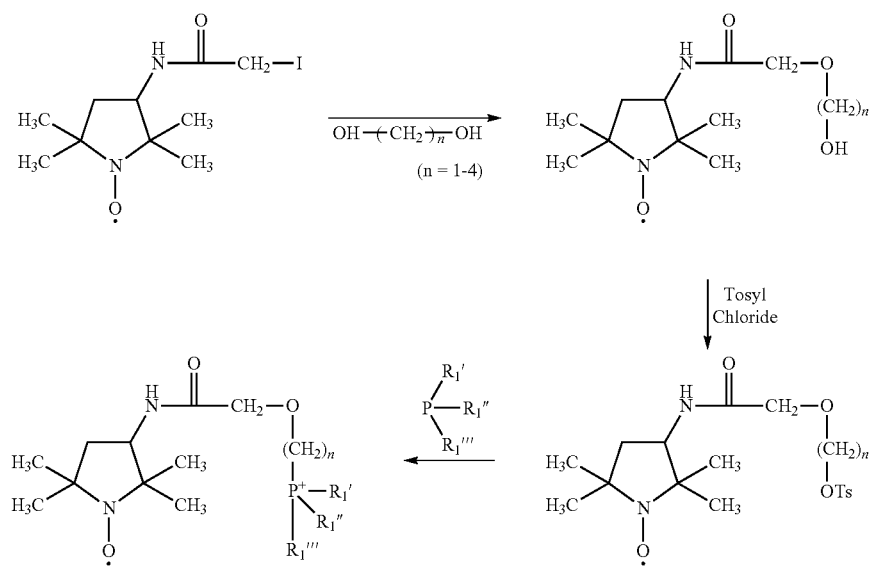

Those of ordinary skill in the art of synthetic chemistry can readily devise other related methods for synthesizing compound comprising Proxyl or Tempol antioxidant groups linked by various moieties to quaternary phosphonium or ammonium cations.

Biological Activity of the Compounds

The salts described above have been found to be potent compounds in a number of in vitro biological assays that correlate to or are representative of human diseases, especially diseases of uncontrolled inflammation and/or cellular proliferation, including various cancers.

The biological activity of the compounds described herein can be measured, screened, and/or optimized by testing the salts for their relative ability to kill or inhibit the growth of various human tumor cell lines and primary tumor cell cultures.

Tumor cell lines that can be employed for such tests include, but are not limited to, known cell lines that model cancers and/or diseases of uncontrolled cellular proliferation, such as:

For Leukemia: CCRF-CEM, HL-60 (TB), K-562, MOLT-4, RPMI-8226, and SR. Lung Cancer: A549/ATCC, EKVX, HOP-62, HOP-92, NCI-H226, NCI-H23, NCI-H322M, NCI-H460, and NCI-H522.

Colon Cancer: COLO 205, HCC-2998, HCT-116, HCT-15, HT-29, KM-12, and SW-620.

CNS Cancer: SF-268, SF-295, SF-539, SNB-19, SNB-75, U-231, U-235 and U-251.

Melanoma: LOX-IMVI, MALME-3M, M-14, SK-MEL-2, SK-MEL-28, SK-MEL-5, UACC-257, and UACC-62.

Ovarian Cancer: IGR-OVI, OVCAR-3, OVCAR-4, OVCAR-5, OVCAR-8, and SK-OV-3.

Renal Cancer: 786-0, A-498, ACHN, CAKI-1, RXF-393, RXF-631, SN12C, TK-10, and U0-31.

Prostate Cancer: DU-145, PC-3 and LNCaP.

Breast Cancer: MDA-MB-468, MCF 7, MCF7/ADR-RES, MDA-MB-231/ATCC, HS578T, MDA-MB-435, MDA-N, BT-549, and T-47D.

Pancreatic Cancer: PANC-1, Bx-PC3 AsPC-1.

After the compounds to be screened have been applied to one or more of the above cancer cell lines, the anti-cancer effectiveness can be gauged using a variety of assay procedures known to those of ordinary skill in the art for measuring the number of live cells in the cultures as a function of time.

One well known procedure employs 3-(4,5-dimethylthiazol-2-yl)-2,5-diphenyltetrazolium bromide ("MTT") to differentiate live cells from dead cells. The MTT assay is based on the production of a dark blue formazan product by active dehydrogenase in the mitochondria of live tumor cells (see M. C. Alley, D. A. Scudiero, A. Monks, M. L. Hursey, M. J. Czerwinski, D. L. Fine, B. J. Abbout, J. G. Mayo, R. H. Shoemaker and M. R. Boyd, Cancer Res., 48, 589, 1988). After exposure of cancer cells to the compounds to be screened for a fixed number of days, only living cells contain active dehydrogenases, and produce dark blue formazan from MTT and are stained. The numbers of live cells can be measured by absorbance of visible light by the formazan at 595 nm. Anti-cancer activity can be reported as percent of the tumor cell growth in a culture treated with a placebo. These MTT assay procedures have an advantage over an in vivo assay with common laboratory animals such as mice, in that results are obtained within a week as opposed to requiring several weeks or months.

These MTT anti-cancer activity screening assay provides data regarding the general cytotoxicity of an individual compound. In particular, as described in the examples herein, active anticancer compounds can be identified by applying the compounds at a concentration of about 10 µM to one or more cultured human tumor cell lines, such as for example leukemia, lung cancer, colon cancer, CNS cancer, melanoma, ovarian cancer, renal cancer, prostate cancer, breast cancer, or pancreatic cancer, so as to kill or inhibit cell growth of the tumor cells.

In some embodiments of the invention, the compounds of the invention are considered to be biologically active for the treatment of a particular cancer if, when they are applied to a culture of one of the above cancer cell lines at a concentration of about 10 μM or less, for a period of at least about 5 days, the growth of the cancer cells is inhibited, or the cancer cells killed to the extent of about 50% or more, as compared to a control not comprising the compound of the invention.

For DNA assay, each culture plate was thawed and equilibrated to room temperature under protection from light. Hoechst dye was then added to each well in 200 μL of high salt TNE buffer (10 mM Tris, 1 mM EDTA, 2 M NaCl [pH 7.4]) at a final concentration of 6.7 μg/mL. After further incubation at room temperature for 2 hours under protection from light, culture plates were scanned on the CytoFluor 2350™ scanner using the 360/460 nm filter excitation and emission set. The DNA fluorescence intensity was used as a measure of cell growth.

In particular, the biological activity of two particular salts whose structures are shown below were assayed for their relevance to the treatment or inhibition of the growth of prostate cancers.

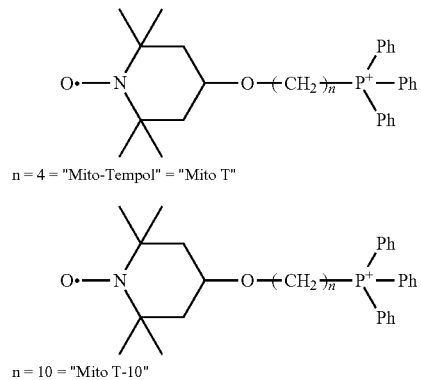

The effects of varying concentrations of Mito-T drug on the growth of LNCaP and PC-3 cells over a period of 4 days was assayed using the Hoechst dye-DNA fluorescence assay described above. In these and all subsequent cell culture studies described below, each data point and its associated error bar are respectively, an average value and the standard deviation of data obtained from six wells of a 96-well plate run in duplicate in three separate sets of experiments.

The results are shown in FIG. 1. Mito-T treatment inhibits the growth of both LNCaP and PC-3 cells, with estimated $IC_{50}$ values of approximately 4 μM and 60 μM, respectively.

The inhibitory effect of MitoT on the oxidative stress level in LNCaP prostate tumor cells can also be determined by the ratio of DCF fluorescence/Hoechst dye-DNA fluorescence (Ripple M O, Henry W F, Rago R P, Wilding G. Prooxidant-antioxidant shift induced by androgen treatment of human prostate carcinoma cells. J Natl Cancer Inst. 1997 Jan. 1; 89(1):40-8). DCFH is oxidized to DCF by ROS to yield easily quantifiable ROS levels monitored by the green fluorescence of the DCF (6-carboxy-2',7'-dichlorofluorescin diacetate) dye, as can be seen in FIG. 2. The DCF fluorescence in LNCaP cells treated with 1 nM of the androgen analog R1881 and normalized with the blue fluorescence of the Hoechst dye-DNA complex in the same cells at varying concentrations of MitoT in order to evaluate the level the oxidative stress per individual cell.

The inhibitory effect of MitoT on the oxidative stress level in LNCaP prostate tumor cells can be determined by the ratio of DCF fluorescence/Hoechst dye-DNA fluorescence. MitoT treatment markedly reduced the oxidative stress in LNCaP cells as determined by DCF fluorescence/DNA fluorescence assay shown in FIG. 3. MitoT treatment effectively and reproducibly reduced the ROS levels in LNCaP cells at concentrations at or above about 1-10 μM. It should be noted that MitoT treatment induced a reduction of oxidative stress determined by DCF assay and mitochondrial function determined by MTT assay, and is parallel to MitoT's effect in the inhibition of prostate tumor cell growth as determined by DNA assay, as shown in FIG. 4, This oxidative stress is probably due to increased lipid peroxidation during apoptotic and/or necrotic cell death (reviewed in 1,2).

Results shown in FIG. 5 clearly demonstrates that MitoT pretreatment at a sublethal dose (1 μM) can also completely block the oxidative stress induced by androgen (R1881) treatment in LNCaP cells. As most published literature demonstrates that androgen is the leading cause of oxidative stress generation and changes (Reviewed by Attia S and Wilding G, Novel Antioxidant Technology for Prostate Cancer Chemoprevention and Treatment. Expert opinion on therapeutic patents, 16(9) 1255-67), which is a primary causative agent of prostate cancer and other prostatic diseases, including, but not limited, to benign prostatic hyperplasia. Thus, the antioxidant spin trapping effect of MitoT treatment is capable of removing one of the most important metabolic products that causes cancer in general and prostate cancer for specific.

FIG. 6 shows that when animals are treated with MitoT, the serum level of MitoT within the first hour of treatment is between 10-20 μg/ml, which is 10-20 times above the level of MitoT required to block androgen induced oxidative stress in LNCaP cells (FIG. 5) and in the concentration range of completely blocking all oxidative stress in the cancer cells. Also, under these treatment conditions, MitoT markedly reduced the oxidative stress in the prostatic lumen of live animals, as observed by Hydroethidine dye oxidation assay in the animal's prostate. Hydroethidine dye was injected into the tail vein of male mice one hour before sacrifice. Hydroethidine shows a typical red fluorescence upon oxidation by ROS. The resected prostate glands of the sacrificed animals were processed and observed under fluorescence microscopy. The data are shown in FIG. 7. As in the case of cell culture studies, the MitoT treated animals did not show any evidence of oxidative stress in the prostate gland Using the Compositions In view of their ability to inhibit the growth of, at least some cancer cell lines in vitro, the compounds described herein can be used to prevent, alleviate or otherwise treat diseases of uncontrolled proliferation in mammals, including humans, such as cancer or precancerous diseases. The compounds described herein can be used for the preparation of medicaments for treating diseases of uncontrolled inflammation, proliferation, cancers, and prostate cancer.

Therefore, in some embodiments, the invention relates to methods of treatment for a disease of uncontrolled cellular inflammation, proliferation, wherein the method comprises administering to a mammal diagnosed as having a disease of uncontrolled cellular inflammation and/or proliferation a compound of the invention or a pharmaceutical composition thereof comprising one or more of the compounds of the invention, in an amount that is effective to treat the disease of uncontrolled cellular inflammation and/or proliferation.

The disease of uncontrolled cellular inflammation and/or proliferation treated can be a hyperplasia or a carcinoma, lymphoma, leukemia, or sarcoma. The types of diseases treated by methods of the invention include but are not limited to Hodgkin's Disease, myeloid leukemia, polycystic kidney disease, bladder cancer, brain cancer, head and neck cancer, kidney cancer, lung cancer, myeloma, neuroblastoma, glioblastoma, ovarian cancer, pancreatic cancer, prostate cancer, skin cancer, liver cancer, melanoma, colon cancer, cervical carcinoma, breast cancer, metastases to the brain or bone, epithelial cancer, and leukemia. The compositions can also be used as regulators in diseases of uncontrolled inflammation and/or proliferation and/or precancerous conditions such as cervical and anal dysplasias, other dysplasias, severe dysplasias, hyperplasias, atypical hyperplasias, and neoplasias.

The compounds of the invention have been found to particularly effective for the treatment of prostate cancers and related neoplasias, including pancreas adenocarcinomas or prostate adenocarcinomas, and/or inhibiting the growth of prostate hyperplasias (non-cancerous) and/or cancers and related neoplasias.

Methods of Treating Diseases with the Salts and/or Compositions

In some embodiments, the inventions described herein relate to methods for treating or inhibiting the recurrence, progression or metastasis, of a cancer or a neoplasia precursor thereof, consisting of administering to a mammal diagnosed as having a cancer or precursor neoplasia thereof, in an amount effective to treat the cancer or inhibit the recurrence, progression, or metastasis of the cancer or precursor neoplasia thereof, one or more pharmaceutically acceptable salts having a cation having the formula

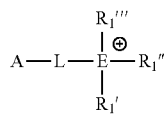

wherein
a) A is an antioxidant moiety comprising one or more nitroxide or hydroxylamine moieties, or a prodrug thereof, having from three to 16 carbon atoms,
b) L is an organic linking moiety comprising 4 to 30 carbon atoms,
c) E is a nitrogen or phosphorus atom,
d) $R_1'$, $R_1''$, and $R_1'''$ are each independently selected organic moieties comprising between 1 and 12 carbon atoms,
wherein E, $R_1'$, $R_1''$, and $R_1'''$ together form a quaternary ammonium or phosphonium cation;
and wherein the salt further comprises is one or more pharmaceutically acceptable anions $X^{m-}$, wherein m is an integer from 1 to 4, in sufficient amount to form the pharmaceutically acceptable salt.

The pharmaceutically acceptable salts of the invention have been found to be particularly effective in treating certain forms inflammation, organ enlargement or cancer, including, but not limited to prostate hyperplasia and/or cancer, colorectal cancer, gastric cancer, renal cancer, skin cancer, head and neck cancer, brain cancer, pancreatic cancer, lung cancer, ovarian cancer, uterine cancer, liver cancer, and breast cancer.

In some embodiments, the invention relates to method for treating, or inhibiting inflammation and benign prostatic hyperplasia or the occurrence, recurrence, progression or metastasis of prostate cancer, consisting of administering to a mammal diagnosed as having prostate disease or cancer or hyperplasia or precursor neoplasia thereof, in an amount effective to treat the disease or cancer or inhibit the occurrence, recurrence, progression, or metastasis of the prostate disease or cancer or precursor neoplasia thereof, one or more pharmaceutically acceptable salts of the invention comprising a cation of Formula (I). In some favored embodiments of the invention, the pharmaceutically acceptable salts have a cation having the formula:

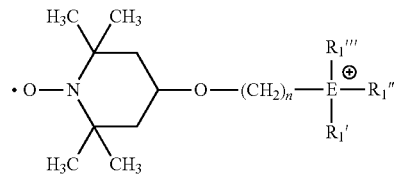

wherein
e) E is a nitrogen or phosphorus atom,
f) $R_1'$, $R_1''$, and $R_1'''$ are each independently selected organic moieties comprising between 1 and 12 carbon atoms,
g) n is an integer between 8 and 12, and
wherein E, $R_1'$, $R_1''$, and $R_1'''$ together form a quaternary ammonium or phosphonium cation; and
the salt also comprises one or more pharmaceutically acceptable anions $X^{m-}$ wherein m is an integer from 1 to 4, sufficient to form the pharmaceutically acceptable salt.

Preparing and Administering the Compounds and Compositions as Pharmaceutical Compositions Although the compounds described herein can be administered as pure chemicals either singularly or plurally, it is preferable to present the active ingredient as a pharmaceutical composition. Thus, another embodiment of the invention is the use of a pharmaceutical composition comprising one or more compounds and/or a pharmaceutically acceptable salt thereof, together with one or more pharmaceutically acceptable carriers thereof and, optionally, other therapeutic and/or prophylactic ingredients. The carrier(s) should be "acceptable" in the sense of being compatible with the other ingredients of the composition and not overly deleterious to the recipient thereof. The pharmaceutical composition, is administered to an animal diagnosed as in need of treatment for a disease of uncontrolled cellular inflammation and/or proliferation, in an amount effective to treat the disease of uncontrolled cellular inflammation and/or proliferation, such as the various cancers and precancerous conditions described herein.

As used herein, "pharmaceutical composition" means therapeutically effective amounts of a pharmaceutically effective compound together with suitable combination of one or more pharmaceutically-acceptable carriers, many of which are known in the art, including diluents, preservatives, solubilizers, emulsifiers, and adjuvants, collectively".

As used herein, the terms "effective amount" and "therapeutically effective amount" refer to the quantity of active therapeutic agent sufficient to yield a desired therapeutic response, without undue adverse side effects, such as toxicity, irritation, or allergic response. The specific "effective amount" will, obviously, vary with such factors as the particular condition being treated, the physical condition of the patient, the type of animal being treated, the duration of the treatment, the nature of concurrent therapy (if any), and the specific formulations employed and the structure of the compounds or its derivatives. In this case, an amount would be deemed therapeutically effective if it resulted in one or more of the following: (a) the prevention of an androgen-mediated or androgen-independent disorder (e.g., prostate cancer); and (b) the reversal or stabilization of an androgen-mediated or androgen-independent disorder (e.g., prostate disease and cancer). The optimum effective amounts can be readily determined by one of ordinary skill in the art using routine experimentation.

Pharmaceutical compositions can be liquids or lyophilized or otherwise dried formulations and include diluents of various buffer content (e.g., Tris-HCI, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thiomersal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, gels, hydrogels, etc, or onto liposomes, microemulsions, micelles, etc.

Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Controlled or sustained release compositions administrable according to the invention include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Other embodiments of the compositions administered according to the invention incorporate particulate forms, protective coatings, protease inhibitors or permeation enhancers for various routes of administration, including parenteral, pulmonary, nasal and oral.

Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding modified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

In yet another method according to the invention, a pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14: 201 (1987); Buchwald et al., Surgery 88: 507 (1980); Saudek et al., N. Engl. J. Med. 321: 574 (1989). In another embodiment, polymeric materials can be used. In yet another embodiment, a controlled release system can be placed in proximity to the therapeutic target, i. e., the prostate, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249: 1527-1533 (1990).

The pharmaceutical preparation can comprise the anti-androgen compound alone, or can further include a pharmaceutically acceptable carrier, and can be in solid or liquid form such as tablets, powders, capsules, pellets, solutions, suspensions, elixirs, emulsions, gels, creams, or suppositories, including rectal and urethral suppositories.

Pharmaceutically acceptable carriers include gums, starches, sugars, cellulosic materials, and mixtures thereof. The pharmaceutical preparation containing the anti-androgen compound can be administered to a patient by, for example, subcutaneous implantation of a pellet. In a further embodiment, a pellet provides for controlled release of anti-androgen compound over a period of time. The preparation can also be administered by intravenous, intra-arterial, or intramuscular injection of a liquid preparation oral administration of a liquid or solid preparation, or by topical application. Administration can also be accomplished by use of a rectal suppository or a urethral suppository.

Though it is not possible to specify a single predetermined pharmaceutically effective amount of the compounds of the invention, and/or their pharmaceutical compositions, for each and every disease condition to be treated, determining such pharmaceutically effective amounts are within the skill of, and ultimately at the discretion of an attendant physician or clinician of ordinary skill In some embodiments, the active compounds of the invention are administered to achieve peak plasma concentrations of the active compound of from typically about 0.1 to about 100 µM, about 1 to 50 µM, or about 2 to about 30 µM. This can be achieved, for example, by the intravenous injection of a 0.05% to 5% solution of the active ingredient, optionally in saline, or orally administered as a bolus containing about 0.5-500 mg of the active ingredient. Desirable blood levels can be maintained by continuous infusion to provide about 0.01-5.0 mg/kg/hr or by intermittent infusions containing about 0.4-15 mg/kg of the active compounds of the invention.

Pharmaceutical compositions include those suitable for oral, enteral, parental (including intramuscular, subcutaneous and intravenous), topical, nasal, vaginal, ophthalinical, sublingual, nasal or by inhalation administration. The compositions can, where appropriate, be conveniently presented in discrete unit dosage forms and can be prepared by any of the methods well known in the art of pharmacy. Such methods include the step of bringing into association the active compound with liquid carriers, solid matrices, semi-solid carriers, finely divided solid carriers or combination thereof, and then, if necessary, shaping the product into the desired delivery system.

The compounds of the invention can have oral bioavailability as exhibited by blood levels after oral dosing, either alone or in the presence of an excipient. Oral bioavailability allows oral dosing for use in chronic diseases, with the advantage of self-administration and decreased cost over other means of administration. Pharmaceutical compositions suitable for oral administration can be presented as discrete unit dosage forms such as hard or soft gelatin capsules, cachets or tablets each containing a predetermined amount of the active ingredient; as a powder or as granules; as a solution, a suspension or as an emulsion. The active ingredient can also be presented as a bolus, electuary or paste. Tablets and capsules for oral administration can contain conventional excipients such as binding agents, fillers, lubricants, disintegrants, or wetting agents. The tablets can be coated according to methods well known in the art., e.g., with enteric coatings.

Oral liquid preparations can be in the form of, for example, aqueous or oily suspensions, solutions, emulsions, syrups or elixirs, or can be presented as a dry product for constitution with water or other suitable vehicle before use. Such liquid preparations can contain conventional additives such as suspending agents, emulsifying agents, non-aqueous vehicles (which can include edible oils), or one or more preservative.

The pharmaceutical preparations administrable by the invention can be prepared by known dissolving, mixing, granulating, or tablet-forming processes. For oral administration, the compounds or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders such as acacia, cornstarch, gelatin, with disintegrating agents such as cornstarch, potato starch, alginic acid, or with a lubricant such as stearic acid or magnesium stearate.

Examples of suitable oily vehicles or solvents are vegetable or animal oils such as sunflower oil or fish-liver oil. Preparations can be effected both as dry and as wet granules or supercritically formulated nanoparticles.

The compounds can also be formulated for parenteral administration (e.g., by injection, for example, bolus injection or continuous infusion) and can be presented in unit dose form in ampules, pre-filled syringes, small bolus infusion containers or in multi-does containers with an added preservative. The compositions can take such forms as suspensions, solutions, or emulsions in oily or aqueous vehicles, and can contain formulatory agents such as suspending, stabilizing and/or dispersing agents. Alternatively, the active ingredient can be in powder form, obtained by aseptic isolation of sterile solid or by lyophilization from solution, for constitution with a suitable vehicle, e.g., sterile, pyrogen-free water, before use.

For parenteral administration (subcutaneous, intravenous, intraarterial, or intramuscular injection), the compounds or their physiologically tolerated derivatives such as salts, esters, N-oxides, and the like are converted into a solution, suspension, or expulsion, if desired with the substances customary and suitable for this purpose, for example, solubilizers or other auxiliaries. Examples are sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

The preparation of pharmaceutical compositions which contain an active component is well understood in the art. Such compositions may be prepared as aerosols delivered to the nasopharynx or as injectables, either as liquid solutions or suspensions; however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like or any combination thereof.

In addition, the composition can contain minor amounts of auxiliary substances such as wetting or emulsifying agents, pH buffering agents which enhance the effectiveness of the active ingredient.

The compounds of the invention comprise cationic antioxidants in the form of a pharmaceutically acceptable salt with pharmaceutically acceptable anions. Pharmaceutically acceptable salts include pharmaceutically acceptable halides such as fluoride, chloride, bromide, or iodide, tribasic phosphate, dibasic hydrogen phosphate, monobasic dihydrogen phosphate, or the anionic forms of pharmaceutically acceptable organic carboxylic acids as acetates, oxalates, tartrates, mandelates, succinates, citrates, and the like. Such pharmaceutically acceptable salts can be readily synthesizes from other salts used for the initial synthesis of the compounds by ion exchange reactions and technologies well known to those of ordinary skill in the art.

Salts formed from any free carboxyl groups on the cationic antioxidant moieties can also be derived from inorganic bases such as, for example, sodium, potassium, ammonium, calcium, or ferric hydroxides, and such organic bases asisopropylamine, trimethylamine, 2-ethylamino ethanol, histidine, procaine, and the like.

For use in medicine, the salts of the anti-androgen compound may be pharmaceutically acceptable salts. Other salts may, however, be useful in the commercial or laboratory preparation of the compounds according to the invention or of their pharmaceutically acceptable salts. Suitable pharmaceutically acceptable salts of the compounds include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid.

In addition, the salts described herein may be provided in the form of nutraceutical compositions where the anti-oxidant properties of the salts prevents the onset of or reduces or stabilizes various disorders, e.g., including inhibiting the occurrence of various forms of cancer, including prostate cancer. The term "nutraceutical," or "nutraceutical composition," for the purposes of this specification, refers to a food item, or a part of a food item, that offers medical health benefits, including prevention and/or treatment of disease. A nutraceutical composition according to the present invention may contain only a cationic antioxidant compound according to the present invention as an active ingredient or, alternatively, may further comprise, in admixture with the aforesaid cationic antioxidant compound, dietary supplements including vitamins, co-enzymes, minerals. herbs, amino acids and the like which supplement the diet by increasing the total intake of that substance.

Therefore, the present invention provides methods of providing nutraceutical benefits to a patient, comprising the step of administering to the patient a nutraceutical composition containing a compound having Formula I or a pharmaceutically acceptable salt thereof. Such compositions generally include a "nutraceutically-acceptable carrier" which, as referred to herein, is any carrier suitable for oral delivery including, but not limited to, the aforementioned pharmaceutically-acceptable carriers. In certain embodiments, nutraceutical compositions according to the invention comprise dietary supplements which, defined on a functional basis, include immune boosting agents, anti-inflammatory agents, anti-oxidant agents, or mixtures thereof.

Although some of the supplements listed above have been described as to their pharmacological effects, other supplements may also be utilized in the present invention and their effects are well documented in the scientific literature.

In general, one of skill in the art understands how to extrapolate in vivo data obtained in a model organism, such as athymic nude mice inoculated with human tumor cell lines, to another mammal, such as a human. These extrapolations are not simply based on the weights of the two organisms, but rather incorporate differences in rates of metabolism, differences in pharmacological delivery, and administrative routes. Based on these types of considerations, a suitable dose will, in alternative embodiments, typically be in the range of from about 0.5 to about 10 mg/kg/day, or from about 1 to about 20 mg/kg of body weight per day, or from about 5 to about 50 mg/kg/day.

The desired dose can conveniently be presented in a single dose or as divided doses administered at appropriate intervals, for example, as two, three, four or more sub-doses per day. The sub-dose, as necessary by one skilled in the art, can itself be further divided, e.g., into a number of discrete loosely spaced administrations.

One skilled in the art will recognize that dosage and dosage forms outside these typical ranges can be tested and, where appropriate, be used in the methods of this invention.

Combinations with Other Active Agents

According to another aspect of the invention, pharmaceutical compositions of matter useful for the treatment of cancer and/or benign prostatic hyperplasia are provided that contain, in addition to the aforementioned compounds, an additional therapeutic agent. Such agents can be chemotherapeutic agents, ablation or other therapeutic hormones, antineoplastic agents, monoclonal antibodies useful against cancers and angiogenesis inhibitors. The following discussion highlights some agents in this respect, which are illustrative, not limitative. A wide variety of other effective agents also can be used.

Among hormones which can be used in combination with the present inventive compounds, diethylstilbestrol (DES), leuprolide, flutamide, hydroxyflutamide, bicalutamide, cyproterone acetate, ketoconazole, abiraterone acetate and amino glutethimide.

Among antineoplastic and anticancer agents that can be used in combination with the inventive compounds, 5-fluorouracil, vinblastine sulfate, estramustine phosphate, suramin and strontium-89. Other chemotherapeutics useful in combination and within the scope of the present invention are buserelin, chlorotranisene, chromic phosphate, cisplatin, cyclophosphamide, dexamethasone, doxorubicin, estradiol, estradiol valerate, estrogens conjugated and esterified, estrone, ethinyl estradiol, floxuridine, goserelin, hydroxyurea, melphalan, methotrexate, mitomycin and prednisone.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A salt comprising one or more cations having the formula:

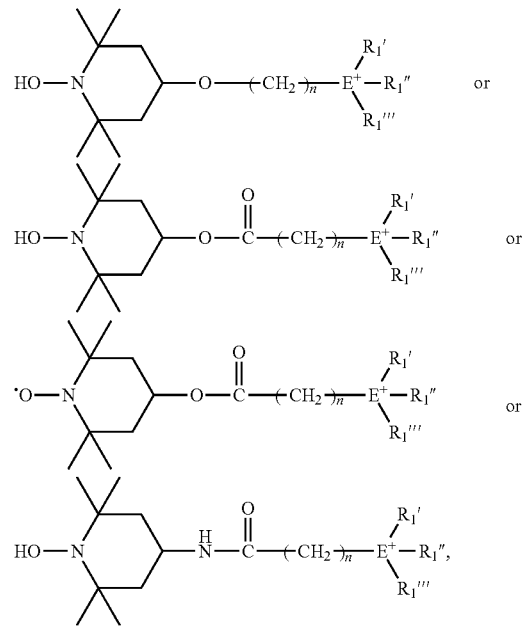

wherein

E is a phosphorus atom, $R_1'$, $R_1''$, and $R_1'''$ are each independently organic moieties comprising between 1 and 12 carbon atoms, n is an integer between 6 and 24, and wherein E, $R_1'$, $R_1''$, and $R_1'''$ together form a quaternary phosphonium cation; and wherein the salt further comprises one or more anions $X^{m-}$ wherein m is an integer from 1 to 4, to form the salt.

2. The salt of claim 1, wherein $R_1'$, $R_1''$, and $R_1'''$ are independently selected from $C_1$-$C_{10}$ alkyl or phenyl moieties;

n is 10; and $X^{m-}$ is a pharmaceutically acceptable anion.

3. A pharmaceutical composition comprising one or more pharmaceutically acceptable salts of claim 1 and one or more pharmaceutically acceptable carriers.

* * * * *